United States Patent
Ellmark et al.

(10) Patent No.: US 12,415,862 B2
(45) Date of Patent: Sep. 16, 2025

(54) METHODS AND COMPOSITIONS

(71) Applicant: ALLIGATOR BIOSCIENCE AB, Lund (SE)

(72) Inventors: Peter Ellmark, Lund (SE); Per Norlen, Limhamn (SE); Karin Hagerbrand, Hjarup (SE)

(73) Assignee: ALLIGATOR BIOSCIENCE AB, Lund (SE)

( * ) Notice: Subject to any disclaimer, the term of this patent is extended or adjusted under 35 U.S.C. 154(b) by 430 days.

(21) Appl. No.: 17/914,603

(22) PCT Filed: Mar. 30, 2021

(86) PCT No.: PCT/EP2021/058351
§ 371 (c)(1),
(2) Date: Sep. 26, 2022

(87) PCT Pub. No.: WO2021/198288
PCT Pub. Date: Oct. 7, 2021

(65) Prior Publication Data
US 2024/0002524 A1    Jan. 4, 2024

(30) Foreign Application Priority Data

Mar. 31, 2020 (GB) .................................... 2004677

(51) Int. Cl.
| | |
|---|---|
| C07K 16/28 | (2006.01) |
| A61K 38/00 | (2006.01) |
| C07K 14/31 | (2006.01) |
| A61K 39/00 | (2006.01) |

(52) U.S. Cl.
CPC .......... *C07K 16/2878* (2013.01); *C07K 14/31* (2013.01); *A61K 38/00* (2013.01); *A61K 2039/505* (2013.01); *C07K 2317/522* (2013.01); *C07K 2317/524* (2013.01); *C07K 2319/43* (2013.01); *C07K 2319/705* (2013.01)

(58) Field of Classification Search
CPC ..... C07K 16/2878; C07K 14/31; A61K 38/00
See application file for complete search history.

(56) References Cited

U.S. PATENT DOCUMENTS

| | | |
|---|---|---|
| 4,816,567 A | 3/1989 | Cabilly et al. |
| 2014/0348836 A1 | 11/2014 | Ellmark et al. |

FOREIGN PATENT DOCUMENTS

| | | |
|---|---|---|
| WO | 2015/091853 A2 | 6/2015 |
| WO | 2017/205738 A1 | 11/2017 |
| WO | 2020/127374 A2 | 6/2020 |

OTHER PUBLICATIONS

Attucci, et al., "EPI-hNE4, a Proteolysis-Resistant Inhibitor of Human Neutrophil Elastase and Potential Anti-Inflammatory Drug for Treating Cystic Fibrosis" J. Pharmoc. Exp. Therap. (2006) 318(2):803-809.
Binz, et al., "High-affinity binders selected from designed ankyrin repeat protein libraries" Nat. Biotech. (2004) 22(5):575-582.
Boerner, et al., "Production of antigen-specific human monoclonal antibodies from in vitro-primed human splenocytes" J. Immunol. (1991) 147(1): 86-95.
Borghouts, et al., "Peptide aptamers: recent developments for cancer therapy" Expert Opin. Biol. Ther. (2005) 5 (6):783-797.
Brinkmann, et al., "The making of bispecific antibodies" mAbs (2017) 9(2):182-212.
Chatterjee, et al., "Internalization and endosomal degradation of receptor-bound antigens regulate the efficiency of cross presentation by human dendritic cells" Blood (2012) 120(10):2011-2020.
Choe, et al., "Fc-Binding Ligands of Immunoglobulin G: An Overview of High Affinity Proteins and Peptides" Materials (2016) 9:994.
Cole, et al., "Human monoclonal antibodies" Molecular and Cellular Biochemistry (1984) 62:109-120.
Cote, et al., "Generation of human monoclonal antibodies reactive with cellular antigens" Proc. Natl. Acad. Sci. (1983) 80:2026-2030.
Cole, et al., "The EBV-Hybridoma Technique and Its Application to Human Lung Cancer" Monoclonal Abs. Cancer Therapy (1985) 77-96.
Dahlen, et al., "Bispecific antibodies in cancer immunotherapy" Therapeutic Advances in Vaccines and Immunotherapy (2018) 6(1):3-17.
Daudey, et al., "Membrane-Fusogen Distance Is Critical for Efficient Coiled-Coil-Peptide-Mediated Liposome Fusion" Langmuir (2017) 33:12443-12452.
Drozdetskiy, et al., "JPred4: a protein secondary structure prediction server" Nucleic Acids Research (2015) 43:W389-W394.
Greenfield, N.J., et al., "Using circular dichroism spectra to estimate protein secondary structure" Nat Protoc. (2006) 1(6):2876-2890.
Hey, et al., "Artificial, non-antibody binding proteins for pharmaceutical and industrial applications" Trends Biotech. (2005) 23(10):514-522.
Hoogenboom, et al., "By-passing immunisation: Human antibodies from synthetic repertoires of germline VH gene segments rearranged in vitro" J. Mol. Biol. (1992) 227:381-388.
Jones, et al., "Replaceing the complementarity-determinig regions in a human antibody with those from a mouse" Nature (1986) 321:522-525.
Kohler, et al., "Continuous cultures of fused cells secrfeting antibodies of predefined specificity" Nature (1975) 256:495-497.

(Continued)

*Primary Examiner* — Amber D Steele
(74) *Attorney, Agent, or Firm* — Robert C. Netter, Jr.; Dann, Dorfman, Herrell & Skillman

(57) ABSTRACT

The present invention provides polypeptides capable of targeting antigens, such as neoantigens, to particular immune cells, and associated therapeutic methods. In particular embodiments, the polypeptides are antibodies or antibody-based polypeptides.

20 Claims, 4 Drawing Sheets

Figure 1:
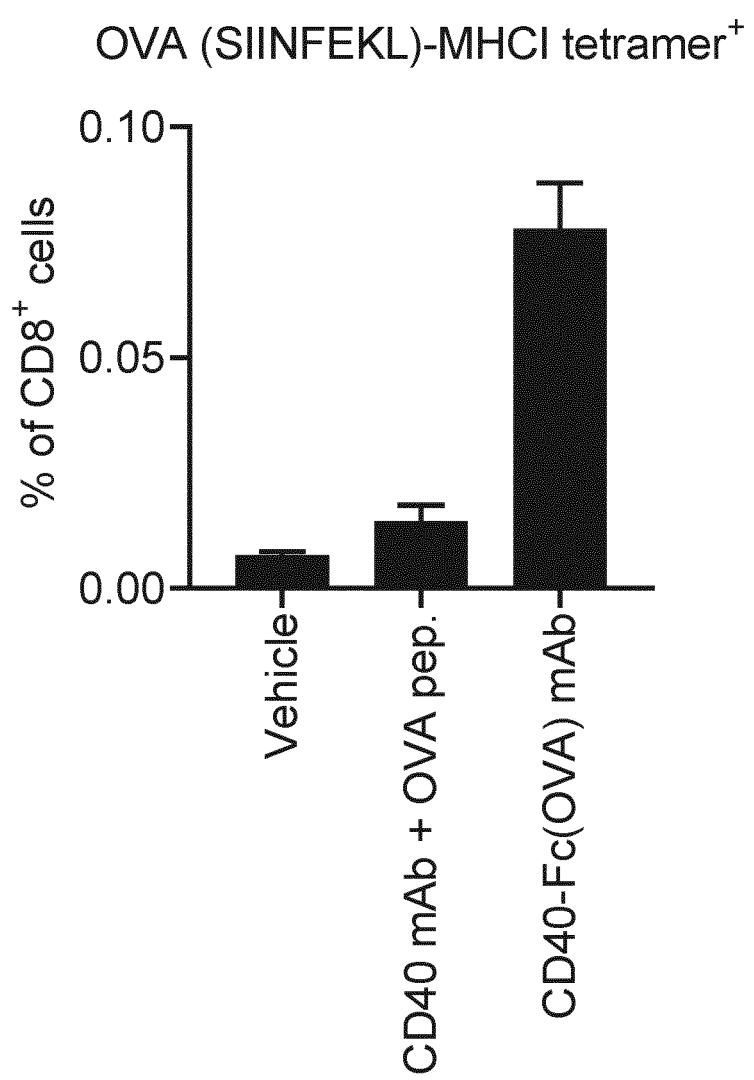

Specification includes a Sequence Listing.

(56) References Cited

OTHER PUBLICATIONS

Kozbor, et al., "Specific Immunoglobulin Production and Enhanced Tumorigenicity Following Ascites Growth of Human Hybridomas" J. Immunol. Methods (1985) 81:31-42.
Krause, et al., "Grafting of thrombopoietin-mimetic peptides into cystine knot miniproteins yields high-affinity thrombopoietin antagonists and agonists" FEBS Journal (2007) 274:86-95.
Marks, et al., "By-passing immunization: Human Antibodies from V-gene Libraries Discplayed on Phage" J. Mol. Biol. (1991) 222:581-597.
Nygren, P.A., "Alternative binding proteins: Affibody binding proteins developed from a small three-helix bundle scaffold" FEBS Journal (2008) 275:2668-2676.
Orlandi, et al., "Cloning immunoglobulin variable domains for expression by the polymerase chain reaction" Proc. Natl. Acad. Sci. (1989) 86:3833-3837.
Picco, et al., "Targeting DNGR-1 (CLEC9A) with antibody/MUC1 peptide conjugates as a vaccine for carcinomas" Eur. J. Immunol. (2014) 44:1947-1955.
Presta, L.G., "Antibody engineering" Current Opinion in Structural Biology (1992) 2:593-596.
Reuter, et al., "Criteria for Dendritic Cell Receptor Selection for Efficient Antibody-Targeted Vaccination" J. Immunology (2015) 194:2696-2705.
Riechmann, et al., "Reshaping human antibodies for therapy" Nature (1988) 332:323-327.
Sanchez-Paulete, et al., "Cancer immunotherapy with immunomodulatory anti-CD137 and anti-PD-1 monoclonal antibodies requires Batf3-dependent dendritic cells" Cancer Discov. (2016) 6(1): 71-79.
Schlehuber, et al., "Lipocalins in drug discovery: from natural ligand-binding proteins to 'anticalins'" Drug Discov. (2005) 10:23-33.
Silverman, et al., "Multivalent avimer proteins evolved by exon shuffling of a family of human receptor domains" Nat. Biotech. (2005) 23(12):1556-1561.
Verhoeyen, et al., "Reshaping Human Antibodies: Grafting an Antilysozyme Activity" Science (1988) 239(4847): 1534-1536.
Walsh, et al., "PASTA 2.0: an improved server for protein aggregation prediction" Nucleic Acids Research (2014) 42:W301-W307.
Wang, et al., "Antigen targeting to dendritic cells with bispecific antibodies" Journal of Immunological Methods (2005) 306:80-92.
Whitlow, et al., "An improved linker for single-chain Fv with reduced aggregation and enhanced proteolytic stability" Protein Engineering (1993) 6:989-995.
Clackson, et al., "Making antibody fragments using phage display libraries" Nature (1991) 352:624-628.
Xu, et al., "Production of bispecific antibodies in "knobs-into-holes" using a cell-free expression system" mAbs (2015) 7:231-242.
Yano, et al., "Coiled-Coil TagProbe System for Quick Labeling of Membrane Receptors in Living Cells" ACS Chem. Biol. (2008) 3:341-345.
Yin, et al., "Functional Specialty of CD40 and Dendritic Cell Surface Lectins for Exogenous Antigen Presentation to CD8+ and CD4+ T Cells" EBioMedicine (2016) 5:46-58.
Zom, et al., "Two in one: improving synthetic long peptide vaccines by combining antigen and adjuvant in one molecule" OncoImmunology (2014) 3:e947892.
Gebauer, et al., "Engineered protein scaffolds as next-generation antibody therapeutics" Current Opinion in Chemical Biology (2009) 13:245-255.
Hurrell, J.G.R., "Monoclonal Hybridoma Antibodies: Techniques and Applications" CRC Press, Inc., Boca Raton, FLA (1982) pp. 1-22.
Sharma, et al., "The future of immune checkpoint therapy" Science (2015) 348:56-61.
Pule, et al., "Artificial T-cell receptors" Cytotherapy (2003) 5(3):211-226.

Z33 = OVA-Z33 [(SIINFEKL)-Z33]

SEQUENCE LISTING

```
<160> NUMBER OF SEQ ID NOS: 70

<210> SEQ ID NO 1
<211> LENGTH: 117
<212> TYPE: PRT
<213> ORGANISM: Artificial Sequence
<220> FEATURE:
<223> OTHER INFORMATION: Antibody 1132/1133 Variable heavy chain (VH)

<400> SEQUENCE: 1

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Ser Tyr Gly Gly Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Asn Phe Gly Met Asp Tyr Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Antibody 1132/1133 Variable light chain (VL)

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Arg Asn Pro Pro
                85                  90                  95

Thr Phe Gly Gln Gly Thr Lys Leu Glu Ile Lys
            100                 105

<210> SEQ ID NO 3
<211> LENGTH: 8
<212> TYPE: PRT
<213> ORGANISM: Artificial Sequence
<220> FEATURE:
<223> OTHER INFORMATION: Antibody 1132/1133 VH CDR1

<400> SEQUENCE: 3

Gly Phe Thr Phe Ser Ser Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Antibody 1132/1133 VH CDR2

<400> SEQUENCE: 4

Ile Gly Ser Tyr Gly Gly Gly Thr
1               5

```
<210> SEQ ID NO 5
<211> LENGTH: 10
<212> TYPE: PRT
<213> ORGANISM: Artificial Sequence
<220> FEATURE:
<223> OTHER INFORMATION: Antibody 1132/1133 VH CDR3

<400> SEQUENCE: 5

Ala Arg Tyr Val Asn Phe Gly Met Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Antibody 1132/1133 VL CDR1

<400> SEQUENCE: 6

Gln Ser Ile Ser Ser Tyr
1               5

<210> SEQ ID NO 7

<400> SEQUENCE: 7

000

<210> SEQ ID NO 8
<211> LENGTH: 9
<212> TYPE: PRT
<213> ORGANISM: Artificial Sequence
<220> FEATURE:
<223> OTHER INFORMATION: Antibody 1132/1133 VL CDR3

<400> SEQUENCE: 8

Gln Gln Tyr Gly Arg Asn Pro Pro Thr
1               5

<210> SEQ ID NO 9
<211> LENGTH: 351
<212> TYPE: DNA
<213> ORGANISM: Artificial Sequence
<220> FEATURE:
<223> OTHER INFORMATION: Antibody 1132/1133 Variable heavy chain (VH)

<400> SEQUENCE: 9
gaggtgcagc tgttggagag cggggggaggc ttggtacagc ctggggggtc cctgcgcctc      60
tcctgtgcag ccagcggatt cacctttagc agctatgcca tgagctgggt ccgccaggct     120
ccagggaagg ggctggagtg ggtctcaggt attggttctt acggtggtgg tacatactat     180
gcagactccg tgaagggccg gttcaccatc tcccgtgaca attccaagaa cacgctgtat     240
ctgcaaatga acagcctgcg tgccgaggac acggctgtat attattgtgc gcgctacgtt     300
aacttcggta tggactattg gggccaggga accctggtca ccgtctcctc a              351

<210> SEQ ID NO 10
<211> LENGTH: 321
<212> TYPE: DNA
<213> ORGANISM: Artificial Sequence
<220> FEATURE:
<223> OTHER INFORMATION: Antibody 1132/1133 Variable light chain (VL)

<400> SEQUENCE: 10
gacatccaga tgacccagtc tccatcctcc ctgagcgcat ctgtaggaga ccgcgtcacc       60
```

```
atcacttgcc gggcaagtca gagcattagc agctatttaa attggtatca gcagaaacca    120
gggaaagccc ctaagctcct gatctatgct gcatccagtt tgcaaagtgg ggtcccatca    180
cgtttcagtg gcagtggaag cgggacagat tcactctca ccatcagcag tctgcaacct     240
gaagattttg caacttatta ctgtcaacag tacggtcgta acccgccac ttttggccag     300 gggaccaagc tggagatcaa a                                              321
```

<210> SEQ ID NO 11
<211> LENGTH: 119
<212> TYPE: PRT
<213> ORGANISM: Artificial Sequence
<220> FEATURE:
<223> OTHER INFORMATION: Antibody 1140/1135 Variable heavy chain (VH)

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Val Tyr Ser Val Phe Asp Tyr Trp Gly Gln Gly
            100                 105                 110

Thr Leu Val Thr Val Ser Ser
        115
```

<210> SEQ ID NO 12
<211> LENGTH: 107
<212> TYPE: PRT
<213> ORGANISM: Artificial Sequence
<220> FEATURE:
<223> OTHER INFORMATION: Antibody 1140/1135 Variable light chain (VL)

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 13
<211> LENGTH: 8
<212> TYPE: PRT

```
<213> ORGANISM: Artificial Sequence
<220> FEATURE:
<223> OTHER INFORMATION: Antibody 1140/1135 VH CDR1

<400> SEQUENCE: 13

Gly Phe Thr Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Antibody 1140/1135 VH CDR2

<400> SEQUENCE: 14

Ile Ser Gly Ser Gly Gly Ser Thr
1               5

<210> SEQ ID NO 15
<211> LENGTH: 12
<212> TYPE: PRT
<213> ORGANISM: Artificial Sequence
<220> FEATURE:
<223> OTHER INFORMATION: Antibody 1140/1135 VH CDR3

<400> SEQUENCE: 15

Ala Arg Gly Pro Val Tyr Ser Ser Val Phe Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Antibody 1140/1135 VL CDR1

<400> SEQUENCE: 16

Gln Ser Ile Ser Ser Tyr
1               5

<210> SEQ ID NO 17

<400> SEQUENCE: 17

000

<210> SEQ ID NO 18
<211> LENGTH: 9
<212> TYPE: PRT
<213> ORGANISM: Artificial Sequence
<220> FEATURE:
<223> OTHER INFORMATION: Antibody 1140/1135 VL CDR3

<400> SEQUENCE: 18

Gln Gln Ser Tyr Ser Thr Pro Tyr Thr
1               5

<210> SEQ ID NO 19
<211> LENGTH: 357
<212> TYPE: DNA
<213> ORGANISM: Artificial Sequence
<220> FEATURE:
<223> OTHER INFORMATION: Antibody 1140/1135 Variable heavy chain (VH)

<400> SEQUENCE: 19
gaggtgcagc tgttggagag cggggggaggc ttggtacagc ctggggggtc cctgcgcctc    60
```

```
tcctgtgcag ccagcggatt cacctttagc agctatgcca tgagctgggt ccgccaggct      120
ccagggaagg ggctggagtg ggtctcagct attagtggta gtggtggtag cacatactat      180
gcagactccg tgaagggccg gttcaccatc tcccgtgaca attccaagaa cacgctgtat      240
ctgcaaatga acagcctgcg tgccgaggac acggctgtat attattgtgc gcgcggtccg      300
gtttactctt ctgttttga ctattgggc cagggaaccc tggtcaccgt ctcctca          357
```

<210> SEQ ID NO 20
<211> LENGTH: 321
<212> TYPE: DNA
<213> ORGANISM: Artificial Sequence
<220> FEATURE:
<223> OTHER INFORMATION: Antibody 1140/1135 Variable light chain (VL)

<400> SEQUENCE: 20

```
gacatccaga tgacccagtc tccatcctcc ctgagcgcat ctgtaggaga ccgcgtcacc       60
atcacttgcc gggcaagtca gagcattagc agctatttaa attggtatca gcagaaacca      120
gggaaagccc ctaagctcct gatctatgct gcatccagtt tgcaaagtgg ggtcccatca      180
cgtttcagtg gcagtggaag cgggacagat ttcactctca ccatcagcag tctgcaacct      240
gaagattttg caacttatta ctgtcaacag agttacagta ccccttatac ttttggccag      300
gggaccaagc tggagatcaa a                                                321
```

<210> SEQ ID NO 21
<211> LENGTH: 117
<212> TYPE: PRT
<213> ORGANISM: Artificial Sequence
<220> FEATURE:
<223> OTHER INFORMATION: Antibody 1150/1151 Variable heavy chain (VH)

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Gly Gly Ser Ser Ser Tyr Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Ser Tyr His Met Asp Tyr Trp Gly Gln Gly Thr Leu
            100                 105                 110

Val Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: Antibody 1150/1151 Variable light chain (VL)

<400> SEQUENCE: 22

Asp Ile Gln Met Thr Gln Ser Pro Ser Ser Leu Ser Ala Ser Val Gly
1               5                   10                  15

```
Asp His Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ser Ala Pro Pro
                85                  90                  95

Thr Phe Gly Gln Gly Thr Lys Leu Glu Ile Lys
            100                 105

<210> SEQ ID NO 23
<211> LENGTH: 8
<212> TYPE: PRT
<213> ORGANISM: Artificial Sequence
<220> FEATURE:
<223> OTHER INFORMATION: Antibody 1150/1151 VH CDR1

<400> SEQUENCE: 23

Gly Phe Thr Phe Ser Ser Tyr Ala
1               5

<210> SEQ ID NO 24
<211> LENGTH: 8
<212> TYPE: PRT
<213> ORGANISM: Artificial Sequence
<220> FEATURE:
<223> OTHER INFORMATION: Antibody 1150/1151 VH CDR2

<400> SEQUENCE: 24

Ile Gly Gly Ser Ser Ser Tyr Thr
1               5

<210> SEQ ID NO 25
<211> LENGTH: 10
<212> TYPE: PRT
<213> ORGANISM: Artificial Sequence
<220> FEATURE:
<223> OTHER INFORMATION: Antibody 1150/1151 VH CDR3

<400> SEQUENCE: 25

Ala Arg Tyr Tyr Ser Tyr His Met Asp Tyr
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Antibody 1150/1151 VL CDR1

<400> SEQUENCE: 26

Gln Ser Ile Ser Ser Tyr
1               5

<210> SEQ ID NO 27

<400> SEQUENCE: 27

000
```

<210> SEQ ID NO 28
<211> LENGTH: 9
<212> TYPE: PRT
<213> ORGANISM: Artificial Sequence
<220> FEATURE:
<223> OTHER INFORMATION: Antibody 1150/1151 VL CDR3

<400> SEQUENCE: 28

Gln Gln Tyr Gly Ser Ala Pro Pro Thr
1               5

<210> SEQ ID NO 29
<211> LENGTH: 351
<212> TYPE: DNA
<213> ORGANISM: Artificial Sequence
<220> FEATURE:
<223> OTHER INFORMATION: Antibody 1150/1151 Variable heavy chain (VH)

<400> SEQUENCE: 29
gaggtgcagc tgttggagag cggggaggc ttggtacagc ctggggggtc cctgcgcctc        60
tcctgtgcag ccagcggatt cacctttagc agctatgcca tgagctgggt ccgccaggct       120
ccagggaagg gctggagtg gtctcaggt attggtggtt cttcttctta cacatcttat        180
gcagactccg tgaagggccg gttcaccatc tcccgtgaca attccaagaa cacgctgtat       240
ctgcaaatga acagcctgcg tgccgaggac acggctgtat attattgtgc gcgctactac       300
tcttaccata tggactattg gggccaggga accctggtca ccgtctcctc a                351

<210> SEQ ID NO 30
<211> LENGTH: 321
<212> TYPE: DNA
<213> ORGANISM: Artificial Sequence
<220> FEATURE:
<223> OTHER INFORMATION: Antibody 1150/1151 Variable light chain (VL)

<400> SEQUENCE: 30
gacatccaga tgacccagtc tccatcctcc ctgagcgcat ctgtaggaga ccacgtcacc        60
atcacttgcc gggcaagtca gagcattagc agctatttaa attggtatca gcagaaacca       120
gggaaagccc ctaagctcct gatctatgct gcatccagtt tgcaaagtgg ggtcccatca       180
cgtttcagtg gcagtggaag cgggacagat ttcactctca ccatcagcag tctgcaacct       240
gaagattttg caacttatta ctgtcaacag tacggttctg ctccgcccac ttttggccag       300
gggaccaagc tggagatcaa a                                                  321

<210> SEQ ID NO 31
<211> LENGTH: 116
<212> TYPE: PRT
<213> ORGANISM: Artificial Sequence
<220> FEATURE:
<223> OTHER INFORMATION: Antibody 1107/1108 Variable heavy chain (VH)

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                        85                  90                  95
Ala Arg Arg Val Trp Gly Phe Asp Tyr Trp Gly Gln Gly Thr Leu Val
                100                 105                 110
Thr Val Ser Ser
        115

<210> SEQ ID NO 32
<211> LENGTH: 107
<212> TYPE: PRT
<213> ORGANISM: Artificial Sequence
<220> FEATURE:
<223> OTHER INFORMATION: Antibody 1107/1108 Variable light chain (VL)

<400> SEQUENCE: 32

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
                20                  25                  30
Leu Asn Trp Tyr Gln Gln Lys Pro Gly Lys Ala Pro Lys Leu Leu Ile
            35                  40                  45
Tyr Ala Ala Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Gly Val Tyr Pro Phe
                85                  90                  95
Thr Phe Gly Gln Gly Thr Lys Leu Glu Ile Lys
                100                 105

<210> SEQ ID NO 33
<211> LENGTH: 8
<212> TYPE: PRT
<213> ORGANISM: Artificial Sequence
<220> FEATURE:
<223> OTHER INFORMATION: Antibody 1107/1108 VH CDR1

<400> SEQUENCE: 33

Gly Phe Thr Phe Ser Ser Tyr Ala
1               5

<210> SEQ ID NO 34
<211> LENGTH: 8
<212> TYPE: PRT
<213> ORGANISM: Artificial Sequence
<220> FEATURE:
<223> OTHER INFORMATION: Antibody 1107/1108 VH CDR2

<400> SEQUENCE: 34

Ile Ser Gly Ser Gly Gly Ser Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Antibody 1107/1108 VH CDR3

<400> SEQUENCE: 35

Ala Arg Arg Val Trp Gly Phe Asp Tyr
```

```
<210> SEQ ID NO 36
<211> LENGTH: 6
<212> TYPE: PRT
<213> ORGANISM: Artificial Sequence
<220> FEATURE:
<223> OTHER INFORMATION: Antibody 1107/1108 VL CDR1

<400> SEQUENCE: 36

Gln Ser Ile Ser Ser Tyr
1               5

<210> SEQ ID NO 37

<400> SEQUENCE: 37

000

<210> SEQ ID NO 38
<211> LENGTH: 9
<212> TYPE: PRT
<213> ORGANISM: Artificial Sequence
<220> FEATURE:
<223> OTHER INFORMATION: Antibody 1107/1108 VL CDR3

<400> SEQUENCE: 38

Gln Gln Tyr Gly Val Tyr Pro Phe Thr
1               5

<210> SEQ ID NO 39
<211> LENGTH: 350
<212> TYPE: DNA
<213> ORGANISM: Artificial Sequence
<220> FEATURE:
<223> OTHER INFORMATION: Antibody 1107/1108 Variable heavy chain (VH)

<400> SEQUENCE: 39
gaggtgcagc tgttggagag cggggaggc ttggtacagc ctgggggtc cctgcgcctc          60 tcctgtgcag ccagcggatt cacctttagc agctatgcca tgagctgggt ccgccaggct       120
ccagggaagg ggctggagtg ggtctcagct attagtggta gtggtggtag cacatactat       180
gcagactccg tgaagggccg gttcaccatc tcccgtgaca attccaagaa cacgctgtat       240
ctgcaaatga acagcctgcg tgccgaggac acggctgtat attattgtgc gcgccgtgtt       300 tgggttttg actattgggg ccagggaacc ctggtcaccg tctcctcagg                   350

<210> SEQ ID NO 40
<211> LENGTH: 321
<212> TYPE: DNA
<213> ORGANISM: Artificial Sequence
<220> FEATURE:
<223> OTHER INFORMATION: Antibody 1107/1108 Variable light chain (VL)

<400> SEQUENCE: 40
gacatccaga tgacccagtc tccatcctcc ctgagcgcat ctgtaggaga ccgcgtcacc        60
atcacttgcc gggcaagtca gagcattagc agctatttaa attggtatca gcagaaacca      120
gggaaagccc ctaagctcct gatctatgct gcatccagtt tgcaaagtgg ggtcccatca      180
cgtttcagtg gcagtggaag cgggacagat ttcactctca ccatcagcag tctgcaacct     240
gaagattttg caacttatta ctgtcaacag tacggtgttt acccgttcac ttttggccag      300
gggaccaagc tggagatcaa a                                                 321
```

```
<210> SEQ ID NO 41
<211> LENGTH: 119
<212> TYPE: PRT
<213> ORGANISM: Artificial Sequence
<220> FEATURE:
<223> OTHER INFORMATION: Antibody G12 (ADC-1013) Variable heavy chain
      (VH)

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Tyr Ile Ser Gly Gly Ser Ser Tyr Ile Phe Tyr Ala Asp Ser Val
    50                  55                  60

Arg Gly Arg Phe Thr Ile Ser Arg Asp Asn Ser Glu Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Arg Gly Gly Ser Gly Met Asp Leu Trp Gly Gln Gly
            100                 105                 110

Thr Leu Val Thr Val Ser Ser
        115

<210> SEQ ID NO 42
<211> LENGTH: 112
<212> TYPE: PRT
<213> ORGANISM: Artificial Sequence
<220> FEATURE:
<223> OTHER INFORMATION: Antibody G12 (ADC-1013) Variable light chain
      (VL)

<400> SEQUENCE: 42

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asn Val Tyr Trp Tyr Gln Gln Leu Pro Gly Thr Ala Pro Lys Leu
        35                  40                  45

Leu Ile Tyr Gly Asn Ile Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Lys Ser
                85                  90                  95

Ile Ser Gly Leu Val Phe Gly Gly Thr Lys Leu Thr Val Leu Gly
            100                 105                 110

<210> SEQ ID NO 43
<211> LENGTH: 10
<212> TYPE: PRT
<213> ORGANISM: Artificial Sequence
<220> FEATURE:
<223> OTHER INFORMATION: Antibody G12 (ADC-1013) VH CDR1

<400> SEQUENCE: 43

Gly Phe Thr Phe Ser Thr Tyr Gly Met His
1               5                   10
```

<210> SEQ ID NO 44
<211> LENGTH: 26
<212> TYPE: PRT
<213> ORGANISM: Artificial Sequence
<220> FEATURE:
<223> OTHER INFORMATION: Antibody G12 (ADC-1013) VH CDR2

<400> SEQUENCE: 44

Gly Lys Gly Leu Glu Trp Leu Ser Tyr Ile Ser Gly Ser Ser Tyr
1               5                   10                  15

Ile Phe Tyr Ala Asp Ser Val Arg Gly Arg
            20                  25

<210> SEQ ID NO 45
<211> LENGTH: 13
<212> TYPE: PRT
<213> ORGANISM: Artificial Sequence
<220> FEATURE:
<223> OTHER INFORMATION: Antibody G12 (ADC-1013) VH CDR3

<400> SEQUENCE: 45

Cys Ala Arg Ile Leu Arg Gly Gly Ser Gly Met Asp Leu
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Antibody G12 (ADC-1013) VL CDR1

<400> SEQUENCE: 46

Cys Thr Gly Ser Ser Ser Asn Ile Gly Ala Gly Tyr Asn Val Tyr
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Antibody G12 (ADC-1013) VL CDR2

<400> SEQUENCE: 47

Gly Asn Ile Asn Arg Pro Ser
1               5

<210> SEQ ID NO 48
<211> LENGTH: 12
<212> TYPE: PRT
<213> ORGANISM: Artificial Sequence
<220> FEATURE:
<223> OTHER INFORMATION: Antibody G12 (ADC-1013) VL CDR3

<400> SEQUENCE: 48

Cys Ala Ala Trp Asp Lys Ser Ile Ser Gly Leu Val
1               5                   10

<210> SEQ ID NO 49
<211> LENGTH: 357
<212> TYPE: DNA
<213> ORGANISM: Artificial Sequence
<220> FEATURE:
<223> OTHER INFORMATION: Antibody G12 (ADC-1013) Variable heavy chain
      (VH)

<400> SEQUENCE: 49

```
gaggtgcagc tgttggagtc tgggggaggc ttggtacagc ctggggggtc cctgagactc      60
tcctgtgcag cctctggatt caccttcagt acttatggca tgcactgggt ccgccaggct     120
ccagggaagg ggctggagtg gctttcatat attagtggtg gtagtagtta catttctac     180 gcagactcag tgaggggccg attcaccatc tccagagaca actccagaaa cgcgctgtat    240
ctgcaaatga acagcctgag agccgaggac acggccgtgt attactgtgc gagaatatta    300
agaggcggga gcggtatgga cctctggggc caaggtacac tggtcaccgt gagctca       357
```

<210> SEQ ID NO 50
<211> LENGTH: 336
<212> TYPE: DNA
<213> ORGANISM: Artificial Sequence
<220> FEATURE:
<223> OTHER INFORMATION: Antibody G12 (ADC-1013) Variable light chain
      (VL)

<400> SEQUENCE: 50

```
cagtctgtgc tgactcagcc accctcagcg tctgggaccc ccgggcagag ggtcaccatc     60
tcttgcactg ggagcagctc aacatcgggg gcgggttaca atgtatactg gtatcagcag    120
ctcccaggaa cggccccaa actcctcatc tatggtaaca tcaatcggcc ctcagggggtc    180 cctgaccgat tctctggctc caagtctggc acctcagcct ccctggccat cagtgggctc    240
cggtccgagg atgaggctga ttattactgt gcagcatggg ataagagcat ttctggtctg    300
gttttcggcg gaggaaccaa gctgacggtc ctaggt                              336
```

<210> SEQ ID NO 51
<211> LENGTH: 33
<212> TYPE: PRT
<213> ORGANISM: Artificial Sequence
<220> FEATURE:
<223> OTHER INFORMATION: Z33

<400> SEQUENCE: 51

Phe Asn Met Gln Gln Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp

<210> SEQ ID NO 52
<211> LENGTH: 21
<212> TYPE: PRT
<213> ORGANISM: Artificial Sequence
<220> FEATURE:
<223> OTHER INFORMATION: K3

<400> SEQUENCE: 52

Lys Ile Ala Ala Leu Lys Glu Lys Ile Ala Ala Leu Lys Glu Lys Ile
1               5                   10                  15

Ala Ala Leu Lys Glu
            20

<210> SEQ ID NO 53
<211> LENGTH: 28
<212> TYPE: PRT
<213> ORGANISM: Artificial Sequence
<220> FEATURE:
<223> OTHER INFORMATION: K4

<400> SEQUENCE: 53

Lys Ile Ala Ala Leu Lys Glu Lys Ile Ala Ala Leu Lys Glu Lys Ile
1               5                   10                  15

Ala Ala Leu Lys Glu Lys Ile Ala Ala Leu Lys Glu
            20                  25

<210> SEQ ID NO 54
<211> LENGTH: 21
<212> TYPE: PRT
<213> ORGANISM: Artificial Sequence
<220> FEATURE:
<223> OTHER INFORMATION: coiled-coil peptide tag E3

<400> SEQUENCE: 54

Glu Ile Ala Ala Leu Glu Lys Glu Ile Ala Ala Leu Glu Lys Glu Ile
1               5                   10                  15

Ala Ala Leu Glu Lys
            20

<210> SEQ ID NO 55
<211> LENGTH: 5
<212> TYPE: PRT
<213> ORGANISM: Artificial Sequence
<220> FEATURE:
<223> OTHER INFORMATION: Linker

<400> SEQUENCE: 55

Gly Ser Ser Ser Ser
1               5

<210> SEQ ID NO 56
<211> LENGTH: 11
<212> TYPE: PRT
<213> ORGANISM: Artificial Sequence
<220> FEATURE:
<223> OTHER INFORMATION: Linker

<400> SEQUENCE: 56

Ser Gly Gly Gly Gly Ser Gly Gly Gly Gly Ser
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Linker

<400> SEQUENCE: 57

Ser Gly Gly Gly Gly Ser Gly Gly Gly Gly Ser Ala Pro
1               5                   10

<210> SEQ ID NO 58
<211> LENGTH: 5
<212> TYPE: PRT
<213> ORGANISM: Artificial Sequence
<220> FEATURE:
<223> OTHER INFORMATION: Linker

<400> SEQUENCE: 58

Asn Phe Ser Gln Pro
1               5

<210> SEQ ID NO 59
<211> LENGTH: 5
<212> TYPE: PRT

```
<213> ORGANISM: Artificial Sequence
<220> FEATURE:
<223> OTHER INFORMATION: Linker

<400> SEQUENCE: 59

Lys Arg Thr Val Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Linker

<400> SEQUENCE: 60

Gly Gly Gly Ser Gly Gly Gly Gly
1               5

<210> SEQ ID NO 61
<211> LENGTH: 10
<212> TYPE: PRT
<213> ORGANISM: Artificial Sequence
<220> FEATURE:
<223> OTHER INFORMATION: Linker

<400> SEQUENCE: 61

Gly Gly Gly Gly Ser Gly Gly Gly Gly Ser
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Linker

<400> SEQUENCE: 62

Gly Gly Gly Gly Ser Gly Gly Gly Gly Ser Gly Gly Gly Gly Ser
1               5                   10                  15

<210> SEQ ID NO 63
<211> LENGTH: 18
<212> TYPE: PRT
<213> ORGANISM: Artificial Sequence
<220> FEATURE:
<223> OTHER INFORMATION: Linker

<400> SEQUENCE: 63

Gly Ser Thr Ser Gly Ser Gly Lys Pro Gly Ser Gly Glu Gly Ser Thr
1               5                   10                  15

Lys Gly

<210> SEQ ID NO 64
<211> LENGTH: 15
<212> TYPE: PRT
<213> ORGANISM: Artificial Sequence
<220> FEATURE:
<223> OTHER INFORMATION: Linker

<400> SEQUENCE: 64

Thr His Thr Cys Pro Pro Cys Pro Glu Pro Lys Ser Ser Asp Lys
1               5                   10                  15

<210> SEQ ID NO 65
<211> LENGTH: 4
```

```
<212> TYPE: PRT
<213> ORGANISM: Artificial Sequence
<220> FEATURE:
<223> OTHER INFORMATION: Linker

<400> SEQUENCE: 65

Gly Gly Gly Ser
1

<210> SEQ ID NO 66
<211> LENGTH: 13
<212> TYPE: PRT
<213> ORGANISM: Artificial Sequence
<220> FEATURE:
<223> OTHER INFORMATION: Linker

<400> SEQUENCE: 66

Glu Ala Ala Lys Glu Ala Ala Lys Gly Gly Gly Gly Ser
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Linker

<400> SEQUENCE: 67

Glu Ala Ala Lys Glu Ala Ala Lys
1               5

<210> SEQ ID NO 68
<211> LENGTH: 4
<212> TYPE: PRT
<213> ORGANISM: Artificial Sequence
<220> FEATURE:
<223> OTHER INFORMATION: tetanus toxin (TTx)

<400> SEQUENCE: 68

Met Thr Thr Glu
1

<210> SEQ ID NO 69
<211> LENGTH: 8
<212> TYPE: PRT
<213> ORGANISM: Artificial Sequence
<220> FEATURE:
<223> OTHER INFORMATION: FLAG-tag

<400> SEQUENCE: 69

Asp Tyr Lys Asp Asp Asp Asp Lys
1               5

<210> SEQ ID NO 70
<211> LENGTH: 8
<212> TYPE: PRT
<213> ORGANISM: Artificial Sequence
<220> FEATURE:
<223> OTHER INFORMATION: OVA peptide

<400> SEQUENCE: 70

Ser Ile Ile Asn Phe Glu Lys Leu
1               5
```

METHODS AND COMPOSITIONS

This application is a § 371 application of PCT/EP2021/058351, filed Mar. 30, 2021, which in turn claims priority to GB Application No. 2004677.7, filed Mar. 31, 2020. The entire disclosure of each of the foregoing applications is incorporated by reference herein.

Incorporated herein by reference in its entirety is the Sequence Listing being concurrently submitted via EFS-Web as a text file named SeqList.txt, created Sep. 23, 2022, and having a size of 26,807 bytes.

FIELD

The present invention relates to the field of targeted antigen delivery to cells, in particular to antigen presenting cells such as dendritic cells.

BACKGROUND

Although immune checkpoint inhibitors have improved the clinical benefit for many cancer patients, there is still a great unmet medical need; especially immunologically "cold" tumors with less T cell infiltration generally do not respond to immune checkpoint inhibitors [1]. Therapeutic cancer vaccines have the potential to increase the tumor-targeting T cell pool, providing a possible treatment for some of these immunologically cold tumors. In addition, any tumor not responding completely to PD-1-targeting therapies could benefit from cancer vaccines.

Therapeutic cancer vaccines have a poor clinical track record, mainly due to the choice of vaccination antigens, which mostly have been tumor-associated self-antigens that do not generate a strong tumor-specific T cell response. The breakthroughs in immunotherapy have shown that for a vaccine to generate a strong T cell response, it is critical to target tumor-specific antigens, e.g. neoantigens.

There are several lines of evidence that demonstrate that neoantigens are critical for obtaining a successful immune response. First, neoantigen-load (mutational burden) of patients' tumors correlate with favorable clinical outcome. Second, tumor neoantigen-specific T cells are expanded by successful immunotherapies (targeting PD-1, CTLA-4). Finally, neoantigen-specific T cells are responsible for the anti-tumor effect of successful immunotherapies.

Thus, the main challenges to address when developing immune cell-targeted therapies are to:
i) provide the right type of immune activation that generates an effective anti-tumor T cell response, and
ii) target tumor antigens, such as neoantigens, that can induce a strong anti-tumor response.

BRIEF SUMMARY OF INVENTION

An issue with current methods of antibody-targeted vaccination is that a new antigen-binding molecule, i.e. antibody, has to be generated for each different antigen that is to be delivered to an immune cell, such as a dendritic cell (DC). The present invention at least addresses this issue and provides an off-the-shelf polypeptide that can be used to deliver a range of antigens to a particular target cell population.

The present invention comprises a polypeptide that in some instances is capable of both optimizing neoantigen uptake by an immune cell and/or cross-presentation of the antigen to T cells. In preferred situations, the tumor of a patient is sequenced to identify suitable personalized neoantigens. These neoantigens may then be produced and attached to, for example, a DC-activating antibody of one embodiment of the invention that promotes uptake of the neoantigen by the DC and at the same time mediates a superior activation of the DC, which in turn allows the DC to cross-present the neoantigens and activate a strong T cell response towards the tumor, and cure the patient.

Antibody-Targeted Vaccination

Antibodies may be selective for DCs and/or other antigen-presenting cells (APC). Antigen fused to a DC-targeting antibody is more efficiently taken up by the DC and subsequently presented to T cells in the context of MHC class I or II compared to free antigen. Consequently, DC-targeted antigen elicits stronger T cell responses compared to free antigen or antigen coupled to an isotype control antibody, and induces superior anti-tumor responses in mouse models [2]. An additional benefit can be gained by incorporating an immune-activating stimulus in the same molecule, for example by targeting an activating DC receptor with an agonistic antibody, since antigen-adjuvant complexes induce superior anti-tumor responses compared to a corresponding mix of antigen and adjuvant [3]. Efficient priming of CD8+ CTL responses is important for generating a productive anti-tumor response, and cDC1 play a prominent role in priming CTL responses for anti-tumor immunity [4]. A productive immune response against a tumor involves both CD8+ and CD4+ T cells, however inducing CD8+ rather than CD4+ T cell responses remains a challenge for cancer vaccines, including neoantigen vaccines. Delivering antigen to a DC population that includes cDC1 is likely to promote the induction of antigen-specific CTL.

The selection of a DC target determines which DC population that is targeted, and how much of the antigen that is taken up and how much is presented on MHC II versus MHC I, the latter being critical for presentation to CD8+ T cells. Further, the choice of DC target also affects the level of DC activation following antigen uptake, which determines if antigen-specific T cells are activated or suppressed. A number of different DC targets have been evaluated for antibody-targeted vaccination, including e.g. CR-1, CLEC9A, DEC-205, CD1c, Dec-1, CD11b, CD11c and CD40 [5-7].

The main advantage with targeting CD40 is that CD40 stimulation activates DC and induces cross-presentation. Despite its poor internalization properties, targeted antigens (i.e. an antibody fused to an antigenic peptide) binding to CD40 induce superior CD8+ T cell responses compared to e.g. DEC-205 [6]. In fact, it was recently demonstrated that CD40 was superior to nine different lectins and scavenger receptors (LOX-1, DC-ASGPR, DCIR, Dectin-1, DEC205, Langerin, MARCO, CLEC6, and DC-SIGN/L) with respect to generating a CD8+ T cell response, using primary human cells in vitro [8]. Further, it was shown that CD40 primarily mediated internalization into early endosomes, which favors antigen processing and cross-presentation to CD8+ T cells.

The goal with the present invention is to provide a drug candidate capable of delivering patient-specific tumor neoantigen to DC, and simultaneously activating the DC, thereby leading to superior priming and activation of neoantigen-specific T cells. The activated T cells will then mediate a superior anti-tumor effect against the neoantigen-expressing tumors. The molecule should mediate DC targeting, activation and antigen internalization, all of which could be achieved using CD40 as DC target. The molecule comprising a CD40-binding domain and a tag-binding domain (for example a peptide-tag binding domain i.e. a domain that binds to a peptide tag) will then be mixed with neoantigens, for example neoantigenic peptides fused to a tag (for example a peptide tag), prior to administration to a patient, resulting in the formation of CD40-neoantigen complexes. Antigen-targeting to DC mediates a more efficient vaccination effect compared to non-targeted antigen, therefore CD40-neoantigen complexes should be superior to a formulation comprising an anti-CD40 antibody and neoantigen peptide, in terms of expansion and/or function of neoantigen-specific T cells and/or anti-tumor effect. By "CD40-neoantigen complex" we mean a complex that forms between 1) the molecule that comprises the CD40-binding domain and the tag-binding domain; and 2) the neoantigen fused to the tag—i.e. it is a complex that targets the neoantigen to cells expressing CD40.

The concept of mixing CD40-tag binding antibodies (i.e. antibody that binds to both CD40 and to a tag) with neoantigen-tag entities (i.e. a neoantigen fused to a tag) to generate CD40-neoantigen complexes provides a flexibility that is not available for current CD40-antigen fusion concepts. For a truly personalized neoantigen vaccination approach, a patient's tumor must first be sequenced and neoantigen epitopes identified, followed by production of the neoantigen. This can be completed in a matter of weeks for peptides, whereas generation of a new antibody or antibody-antigen fusion protein would take more than a year, making it impossible to use as a personal neoantigen vaccine. The CD40-tag antibodies (i.e. capable of binding to CD40 and to the tag) on the other hand would be available as an off-the-shelf product, ready to be mixed with the tagged personal neoantigens (for example antigenic peptides) as soon as they have been synthetized. Further, the CD40-tag antibodies could be mixed with tagged antigens that encompass several neoantigen epitopes. Vaccinating against one neoantigen epitope is generally not sufficient to induce a long-lasting anti-tumor effect, and several neoantigen epitopes will likely be needed to elicit a strong anti-tumor response. In this fashion, the invention addresses limitations with the currently available antibody-antigen fusion proteins.

DETAILED DESCRIPTION OF THE INVENTION

The invention provides a polypeptide molecule that in some embodiments is an antibody, or is an antibody-based molecule, that is able to bind to an immune cell such as a dendritic cell, and is also able to bind to a tag, for example a peptide tag. The tag, for example the peptide tag in preferred embodiments is part of an antigenic peptide or peptide fragment, and in this way a single polypeptide or antibody can be used to target a diverse array of antigens to a particular cellular target. It will be clear however that the tag, for example the peptide tag can be part of any larger peptide or polypeptide, and the polypeptide of the invention can be used to direct any peptide or polypeptide to an immune cell population.

Also encompassed by the present invention is an antibody, or is an antibody-based molecule, that is able to bind to an immune cell such as a dendritic cell, and is also able to bind to a non-peptide tag.

The present invention provides a polypeptide comprising at least one immune cell binding domain and at least one tag binding domain,
   wherein the at least one immune cell binding domain is capable of specifically binding to an immune cell target; and
   wherein the at least one tag binding domain is capable of specifically binding to a tag, for example a peptide tag, wherein the tag, for example the peptide tag is not derived from tetanus toxin.

By the term "binding domain" we include the meaning of any peptide sequence that is capable of binding or associating with a second entity. In the case of the immune cell binding domain, the domain is able to bind specifically to a target on an immune cell; and in the case of the tag binding domain, the domain is able to specifically bind to a tag, for example a peptide tag.

By "bind specifically" we include the meaning that the domain binds to its target in a manner that can be distinguished from binding to non-target domains (i.e. off-targets). For example, a domain that binds specifically may refer to a domain that binds with higher specificity for the intended target compared with that of a non-intended target. Specificity can be determined based on dissociation constant through routine experiments. A domain being "specific for" a target is intended to be synonymous with a domain "directed against" said target.

Preferably the binding domains will bind only to its respective target, i.e. the immune cell target or the tag, for example the peptide tag, and will not bind to any other molecule in the environment, for example in the human body. However, it will be appreciated that some degree of off-target binding may be tolerated, and the skilled person will understand how to determine whether a particular binding activity is of the required specificity or not.

The immune cell binding domain is the portion of the polypeptide that directs or targets the polypeptide of the invention to the desired immune cell, and requires the immune cell binding domain to be able to bind specifically to a particular target on the desired immune cell.

The polypeptide of the invention may comprise a single immune cell binding domain, or may comprise more than one immune cell binding domain. For example, a typical monospecific antibody comprises two variable regions, each capable of binding to the same specific target. In this case, where the target is an immune cell target, the antibody would comprise two immune cell binding domains. The skilled person will be aware of different antibody formats, including those described herein, and will understand that antibody engineering can result in a wide variety of different molecules, with different valences and different specificities.

In one embodiment therefore the polypeptide of the invention may comprise at least 1, 2, 3, 4, 5, 6 or more immune cell binding domains.

In the present invention, where the polypeptides of the invention comprise more than one immune cell binding domain, each of the immune cell binding domains bind to the same target feature or molecule on the immune cell. For example, where the polypeptide comprises two immune cell binding domains, each binding domain binds to the same feature of molecule on the immune cell. This does not necessarily mean however that each of the immune cell binding domains binds to the same epitope. It is possible for a single target, for example an immune cell surface polypeptide, to comprise a number of epitopes. Polypeptides that comprise at least two immune cell binding domains, for example, wherein each binding domain binds to a different epitope of the same target molecule, are therefore encompassed within the invention.

In some embodiments, the polypeptide of the invention may be bi-specific with respect to the immune cell target binding domain, i.e. the polypeptide may comprise at least two different immune cell target binding domains, each capable of binding to a different immune cell target—the different immune cell targets may be present on the same immune cell, or may be targets associated with different immune cells. Similarly, the polypeptide can comprise more than 2, for example 3 or 4 or more different immune cell targeting domains, each binding to a different immune cell target—which may be on the same or different immune cells.

The tag binding domain, for example the peptide tag binding domain of the polypeptide of the invention is the domain that specifically binds to a tag, for example a peptide tag which is part of a larger peptide or polypeptide, and comprises for example an antigen or neoantigen, which it is desirable to target to the immune cell.

In preferred embodiments, the tag is a peptide tag and is expressed as part of a larger peptide or polypeptide and is an integral part of the larger peptide or polypeptide, such as an antigen or neoantigen, i.e. in such embodiments the tagged antigen is a single peptide that comprises both the tag and the antigen.

In other embodiments the tag, for example a peptide tag may be conjugated to a larger peptide or polypeptide, following expression of the larger peptide or polypeptide. For example, the peptide tag may be conjugated to the larger peptide or polypeptide (e.g. a larger peptide or polypeptide that comprises an antigen or neoantigen) through e.g. a GSSSS linker or a cleavable valine-citrulline linker. However, in all embodiments, the peptide tag is not derived from tetanus toxin. For example, a tag derived from the tetanus toxin (TTx), such as MTTE [SEQ ID NO: 68], is not encompassed within the meaning of "tag" or "peptide tag" as used herein.

The concept of "tags" is well known in the molecular biology field, where it is routine to express a peptide or polypeptide sequence of interest wherein the sequence has been extended to include a relatively short additional sequence, encoding the tag. Applications using tagged peptides typically employ an antibody or antibody derived fragment, capable of specifically binding to the tag. Similarly, in a preferred embodiment of the invention, the tag binding domain is an antibody or antibody derived fragment, and binds specifically to the tag. It will be clear to the skilled person that any peptide sequence capable of being specifically recognized by an antibody, i.e. capable of inducing the production of antibodies, can be considered a peptide tag. Examples of suitable peptide tags include the FLAG-tag comprising the amino acid sequence DYKDDDDK [SEQ ID NO: 69], and the skilled person will be aware of other suitable peptide tags such as V5-tag, Myc-tag, HA-tag, Spot-tag, T7-tag and NE-tag.

In one embodiment, the peptide tag is a 33 amino acid sequence as follows:

Z33:
[SEQ ID NO: 51]
FNMQQQRRFYEALHDPNLNEEQRNAKIKSIRDD or a sequence with at least 80%, 85%, 90%, 95%, 98% or 100% sequence identity to SEQ ID NO: 51 and wherein the tag retains the ability to bind to the Fc region.

The antigen or neoantigen may be tagged with a non-peptide tag, for example any moiety that acts as a binding partner for the second specific binding domain. Thus, a non-peptide tag can be any chemical entity with which a second or further entity has affinity. The tag can be selected from, for example, any organic molecule, a small molecule, or a hapten. Tags can for example take the form of nucleic acids, for example aptamers. Tags as described herein are typically short peptide sequences (i.e. sequences of amino acids). In preferred embodiments the tags described herein are peptide or protein tags, for example short sequences of amino acids. The tag can be of any sequence provided it is able to be bound, preferably specifically bound by the tag binding domain of the polypeptide of the invention. Accordingly, in preferred embodiments the tag is a peptide tag, and the corresponding binding domain is a peptide tag binding domain.

By a peptide tag binding domain we mean that the binding domain binds to a peptide tag. It is of course apparent that the binding domain itself will be comprised of amino acids and be considered to be a peptide, since it is part of the polypeptide of the invention.

The antigen or neoantigen can be any antigen or neoantigen. In preferred embodiments the antigen or neoantigen is a peptide or protein antigen or neoantigen. In further preferred embodiments, the tag and the antigen are both peptide antigens, allowing the expression of a tagged antigen as a single peptide. In some embodiments a linker may be present between the sequence encoding the antigen to be delivered to the immune cell and the sequence encoding the tag.

For peptide tags, the term "peptide" is not construed as limited to a certain size or length of amino acids. For example, a peptide tag could be considered a protein, polypeptide, or multiple subunits thereof and simply indicates that the tag comprises a series of amino acids.

In some embodiments the tag binding domain binds to a peptide tag that is less than 100 amino acids in length, for example less than 90, 80, 70, 60, 50, 40, 30, 20 or less than 10 amino acids in length.

The tag, for example the peptide tag, and the tag binding domain, for example the peptide tag binding domain, can be considered to be binding partners and can essentially comprise any pair of entities, for example a pair of peptides, that are capable of specifically interacting with one another.

In some embodiments, peptides suitable for use as a peptide tag in the present invention may be considered in the field to bind to a probe. For example, the pair of peptides K3 ((KIAALKE)×3) [SEQ ID NO: 52] (KIAALKEKIAALKEKIAALKE) or K4 ((KIAALKE)×4) [SEQ ID NO: 53] (KIAALKEKIAALKEKIAALKEKIAALKE) are considered in some publications to bind to the coiled-coil peptide tag E3 ((EIAALEK)×3) [SEQ ID NO: 54] (EIAALEKEIAALEKEIAALEK), which in interaction with K3 ((KIAALKE)×3) [SEQ ID NO: 52] or K4 ((KIAALKE)×4) [SEQ ID NO: 53] is considered to be a probe (Daudey et al., 2017; Yano et al., 2008).

Accordingly, in some embodiments, the peptide tag comprises E3 ((EIAALEK)×3), and the peptide tag binding domain of the polypeptide of the invention comprises K3 ((KIAALKE)×3) or K4 ((KIAALKE)×4). It will be clear that in this instance, and since the E3 ((EIAALEK)×3), K3 ((KIAALKE)×3) and K4 ((KIAALKE)×4) sequences are relatively small, the location of K3 ((KIAALKE)×3) or K4 ((KIAALKE)×4) and E3 ((EIAALEK)×3) is interchangeable. For instance, in one embodiment, the peptide tag binding domain of the polypeptide of the invention comprises K3 ((KIAALKE)×3) or K4 ((KIAALKE)×4), and consequently has the ability to bind to a peptide, for example an antigen peptide or neoantigen peptide, that has been tagged with the E3 ((EIAALEK)×3) peptide; in other embodiments the peptide tag binding domain of the polypeptide of the invention comprises E3 ((EIAALEK)×3), and consequently has the ability to bind to a peptide, for example an antigen peptide or neoantigen peptide, that has been tagged with the peptide K3 ((KIAALKE)×3) or K4 ((KIAALKE)×4).

Such a tag/probe embodiment can be adapted to alternative tag/probe partners, provided there is a degree of affinity between the tag present on the antibody and the probe present on the antigen (or vice versa). The formation of such complexes ex vivo means there is less of a requirement for the tag/probe interaction to be specific to reduce risk of off-target effects provided they bind with strong enough affinity that upon in vivo administration the antigen/probe (or antigen/tag in the alternative) does not dissociate, thereby leaving both components open to binding with alternative targets. Thus, suitable tag/probe partners will have specificity and/or bind with sufficient affinity to maintain complexes in vivo.

Again, such an approach allows for the production of an off-the-shelf product that can be mixed with one or more tagged antigens, for example one or more tagged personalized neoantigen peptides and administered to patients to induce a personal neoantigen-specific T cell response.

Preferably the tag, for example the peptide tag towards which the tag binding domain, for example the peptide tag binding domain of the polypeptide of the invention is directed is a non-human peptide, to avoid unwanted immune responses.

It will be appreciated that in some instances it will be desirable to target more than one tagged antigen to the same immune cell. Accordingly, the polypeptide of the invention may comprise more than one tag binding domain, for example more than one peptide tag binding domain. For example, the polypeptide of the invention may comprise 1, 2, 3, 4 or more tag binding domains, for example peptide tag binding domains.

In some instances, it is beneficial if, where there is more than one tag binding domain, for example peptide tag binding domain present, the tag binding domains, for example the peptide tag binding domains, all have specificity for the same tag (for example specificity for the same peptide tag). In this way for example it is possible to "load" the polypeptide of the invention with multiple copies of the tagged antigen (for example peptide tagged antigen) to be delivered. Alternatively, it may be beneficial for several different neoantigens (for example different neoantigen peptides) to be tagged with the same tag. This strategy would allow for the polypeptide of the invention to be "loaded" with multiple different peptides comprising multiple different antigens.

In other situations, it may be beneficial for one or more of the tag binding domains (for example the peptide tag binding domains) to have specificity for a different tag (for example a peptide tag), so that the polypeptide of the invention can be "loaded" with a range of tagged antigens to be delivered. Alternatively, it may be beneficial for several different neoantigens (for example different neoantigen peptides) to be present sequentially in one long peptide that is tagged with a single tag for example a single peptide tag.

For example, in some embodiments, the polypeptide of the invention comprises at least 1, 2, 3, 4 or more tag binding domains (for example peptide tag binding domains), wherein each of the tag binding domains (for example peptide tag binding domains) has specificity for the same tag (for example peptide tag).

In other embodiments, the polypeptide of the invention comprises at least one tag binding domain (for example peptide tag binding domain) with specificity for a first tag (for example a first peptide tag), and at least one tag binding domain (for example peptide tag binding domain) with specificity for a second tag (for example a second peptide tag). In yet other embodiments, the polypeptide of the invention comprises at least one tag binding domain (for example peptide tag binding domain) with specificity for a first tag (for example a first peptide tag), and at least one tag binding domain (for example peptide tag binding domain) with specificity for a second tag (for example second peptide tag), and at least one tag binding domain (for example peptide tag binding domain) with specificity for a third tag (for example a third peptide tag). In yet other embodiments, the polypeptide of the invention comprises at least one tag binding domain (for example peptide tag binding domain) with specificity for a first tag (for example a first peptide tag), and at least one tag binding domain) for example peptide tag binding domain) with specificity for a second tag (for example a second peptide tag), and at least one tag binding domain (for example peptide tag binding domain) with specificity for a third tag (for example a third peptide tag), and at least one tag binding domain (for example peptide tag binding domain) with specificity for a fourth tag (for example a fourth peptide tag).

As will be apparent, the polypeptides and methods described herein allow particular tagged antigens, such as tagged peptides that comprise one or more antigens to be targeted or directed towards a specific set of immune cells. The skilled person will be aware that various immune cells express different polypeptides and other cell surface molecules and it is routine in the field to classify the different populations of immune cells into subpopulations, based on the expression of one or more polypeptides. The polypeptides of interest are often located on the immune cell surface. In one embodiment, the immune cell binding domain binds to a molecule, for example a polypeptide, that is located on the surface of the target immune cell.

Some cell surface molecules are receptor molecules, which once ligated by, for example, a polypeptide or antibody directed against said receptor molecules, results in a particular function. The ligation of receptor molecules may be by an agonist or antagonist of said receptor. For example, once the CD40 receptor, which can be found on DC, is bound by an agonist, for example an anti-CD40 antibody, the DC is activated. Accordingly, the choice of immune cell target can not only ensure efficient delivery of the tagged peptide, for example tagged antigen, to the immune cell, but can enable other advantageous functions to be activated, enhanced and/or performed, such as activation of the immune cell, enhancement of cytokine release (or enhancement of other ongoing immune cell functions) and/or internalisation of the tagged antigen.

One particular use for the present invention, and as described herein, is in the targeting of antigenic peptides to antigen presenting cells (APC). The skilled person will be aware that these immune cells, which include dendritic cells (DC), B cells and macrophages, are able to internalise components, such as polypeptides, and present fragments of the molecule on the cell surface, in complex with MHCI or MHCII molecules. The presentation of antigenic fragments on MHCI and MHCII molecules activates the innate and adaptive immune responses. It is considered that the present invention has particular utility in activating the innate and adaptive immune response through the targeted delivery of antigens to immune cells, and in particular APC such as those described here, including DC.

DC are professional APC that play a central role in the induction and regulation of adaptive immune responses, including the induction of cytotoxic T lymphocyte (CTL)

responses. DC can be either plasmacytoid DC (pDC), which mainly reside in the blood and lymphoid organs and are capable of secreting large amounts of cytokines, such as type I interferon, upon activation, and conventional DC (cDC).

By "dendritic cell", we include both conventional dendritic cells (cDCs, also known as classical dendritic cells) and plasmacytoid dendritic cells (pDCs). cDCs include both cDC1 and cDC2. By "dendritic cells", we also include both immature dendritic cells and mature, activated, dendritic cells.

As discussed above, the selection of DC target determines which DC population that is targeted, how much of the antigen that is taken up and how much is presented on MHC II or MHC I, the latter being critical for cross-presentation to CD8+ T cells.

CD40 is a cell-surface expressed glycoprotein that belongs to the tumor necrosis factor receptor (TNFR) superfamily and plays a central role in the immune system. It is expressed on a variety of immune cells, such as B cells, DC, monocytes and macrophages, but also on other normal tissues including epithelial cells, endothelial cells and fibroblasts, as well as several tumor types, e.g. on B cell lymphomas and carcinomas. Activation of CD40 on DC results in an anti-tumor immune response via tumor-specific T effector cells. CD40 agonists trigger effective anti-tumor responses in pre-clinical models.

Pre-clinical studies have demonstrated proof of concept for agonistic anti-CD40 antibody treatment of several cancer types, including lymphomas, melanoma, hepatoma, osteosarcoma, renal cell carcinoma, breast cancer and bladder cancer. In addition, humanized or human anti-CD40 antibodies have been evaluated in a number of pre-clinical models and consistently demonstrated anti-tumor effects. Notably, SGN-40, a humanized CD40 monoclonal antibody with partial agonistic effects was evaluated using B cell lymphoma models (Raji and Ramos) in severe combined immunodeficiency (SCID) mice, and demonstrated effects on tumor growth and survival with complete response in approximately 50% of treated mice. CP-870,893, a human agonistic anti-CD40 antibody, showed anti-tumor effects against B cell lymphoma, breast, colon, prostate, and pancreatic cancer in SCID mice. Efficacy was observed in CD40 positive as well as in CD40 negative tumors, thus demonstrating the ability of CP-870,893 to enhance anti-tumor immunity.

TLR3 is part of the Toll-like receptor family and acts as a receptor for danger signals in the form of double-stranded RNA that may be a form of genetic information derived from viruses. Ligation of TLR3 on a DC initiates inflammatory signaling via IRF3 and NE-κB, which activates the DC. Polyinosinic-polycytidylic acid (poly I:C) is a commonly used ligand of TLR3.

Both B cells and DC express high levels of CD40 and may also function as APC. However, it has been demonstrated that DC rather than B cells, macrophages or monocytes are important for generation of antigen-specific T cell responses. These cell populations will, however, act as a sink and may affect the biodistribution.

Other additional DC-markers include: XCR-1, CLEC9A, DEC-205, CD1c, Dec-1. Targeting CLEC9A would confer potential advantages since it is a death cell marker and antigen taken up by this receptor ends up in early endosomes and is more likely to result in cross-presentation to CD8+ T cells. CLEC9A is selectively expressed on cross-presenting DC and may be superior to the more widely tested DEC-205 when it comes to inducing CD8+ T cell activation.

Accordingly, in some embodiments the immune cell is an APC. In some embodiments the immune cell is an APC and is selected from the group comprising or consisting of a DC, B cell or a macrophage. In preferred embodiments, the immune cell is a DC; even more preferred is cDC1.

Polypeptides of the present invention may, in some embodiments, be directed to an immune cell target that is capable of mediating any one or more of: (a) activation of the immune cell (including enhancement of an immune cell activity or function); (b) internalisation of the polypeptide; and/or (c) recruitment of DCs, in particular recruitment of conventional type I dendritic cells (cDC1). For example, an immune cell target that is capable of DC activation includes, but is not limited to, CD40 and TLR3.

In some embodiments, the immune cell target may facilitate internalization of the ligand. By internalizing the polypeptides of the present invention, the antigen of interest is capable of being processed by the immune cell in order to be presented on MHC. Examples of immune cell targets that facilitate internalization include, but are not limited to, CLEC9A and DEC-205. CLEC9A is a C-type lectin receptor involved in sensing necrotic cells, and DEC-205 is a type I cell surface protein expressed primarily by DC.

In some embodiments, the immune cell target may facilitate recruitment of DC, preferably recruitment of cDC1. For example, the immune cell target may be XCR1.

cDC can be found in tissues throughout the body, and in lymphoid organs. cDC in tissues capture antigen, transport it through the lymphatic system into draining lymph nodes, and present it to T cells. cDC that reside in lymphoid organs can also capture antigen, which may have diffused to the organ through the lymphatics, and present this to T cells. cDC can be further divided into two subsets, sometimes termed cDC1 and cDC2. Transcriptional profiling has shown these subsets to be conserved between mice and humans. cDC1 express the chemokine receptor XCR1, which allows them to localize close to XCL1-producing CD8+ T cells in lymphoid tissues, and the dead cell receptor CLEC9A. They are specialized at cross-presenting antigen to CD8+ T cells on MHC I and are required for the priming of CTL responses against TAA in mice. Human cDC1 display superior cross-presenting abilities in some, but not all, in vitro settings compared to other human DC subsets. Uptake of exogenous antigen, such as TAA, in DC is primarily accomplished by receptor-mediated endocytosis. Cross-presentation of exogenous antigen is favored by a relatively high endosomal pH, and routing of antigen to early rather than late endosomes. While high endosomal pH is a characteristic of cDC1, which endosomal compartment the antigen is targeted to depend on the endocytic receptor engaged.

While pDC are generally not very efficient at presenting antigen to T cells, targeting antigen to uptake receptors on pDC can lead to effective cross-presentation to CD8+ T cells.

In some embodiments, the combination of the polypeptide comprising at least one immune cell binding domain and at least one tag binding domain, and the tagged antigen (for example a peptide comprising both the tag and the antigen or neoantigen), when administered to a mammal, for example to a mouse or a human, results in a superior expansion of antigen/neoantigen-specific immune cells, for example CD8+ T cells, compared to treatment with both 1) a polypeptide that comprises the immune cell binding domain but lacks the at least one tag binding domain and 2) the tagged peptide, for example administration of an anti-CD40 antibody (that lacks the tag binding domain) and an antigen/neoantigen peptide separately (i.e. where the antibody and antigen is unable to form a complex). For example, this results in at least a 1.5 fold increase in expansion of antigen/neoantigen-specific immune cells such as CD8+ T cells, or at least a 1.75, 2, 2.25, 2.5, 2.75, 3, 3.25, 3.5, 3.75, 4, 4.5, 5, 5.5, 6, 6.5, 7, 8, 9 or 10 fold increase, for example when administered to a mammal such as a mouse or a human, for example when the agents (as a complex, or administered separately in the absence of the ability to form a complex, i.e. in the absence of the peptide tag, or the peptide tag binding domain) are administered on two occasions with 7 days between, and for example where viable CD45+ CD3+ CD8+ antigen/neoantigen-MHCI tetramer+ T cells are analysed seven days after the second treatment.

In addition or instead of the above method, to determine whether a particular polypeptide having at least one immune cell binding domain and at least one tag binding domain is able to target the tagged molecule, for example a tagged antigen, to a relevant cell population, an in vitro experiment can be performed where the tagged molecule, for example tagged antigen is fluorescently labelled. The labelled antigen is mixed with the immune cell targeting polypeptide, followed by incubation with relevant immune cells. The amount of fluorescently labelled antigen bound to the cells could then be detected by, for example, flow cytometry or fluorescence microscopy.

Accordingly, in one embodiment, the polypeptide of the invention results in the localization of a fluorescently labelled molecule, for example antigen, tagged with the corresponding tag (i.e. the tag to which the tag binding domain binds) to the surface of the immune cell (i.e. the corresponding immune cell to which the immune cell binding domain binds), for example when the polypeptide of the invention is first incubated with the fluorescently labelled tagged molecule (e.g. fluorescently labelled tagged antigen) followed by incubation with the immune cell.

The skilled person will be aware of various peptide-based means of targeting a polypeptide specifically to a molecule, the most commonly used of these being antibody-based means. Standard antibodies typically comprise a single, constant region (Fc), and two variable regions which provide target specificity. In a typical monospecific antibody, each of the two variable regions are identical and directed towards the same epitope on the same target, i.e. they are bivalent for the same target, i.e. monospecific.

Bispecific antibodies have been produced.

The term "bispecific" as used herein means the polypeptide is capable of specifically binding at least two different target entities. Bispecific polypeptides, e.g. antibodies, targeting two targets, have the potential to induce specific activation of the immune system in locations where both targets are over expressed.

The number of formats engineered is vast and the formats can be grouped according to their general architecture. Brinkmann and Kontermann have proposed a classification of 19 groups (see Brinkmann & Kontermann, 2017, mAbs. 9:182-212). The major differences between the groups are in regard to their symmetry, their target valency, their components and the position of these.

Different properties are generally acknowledged for different bispecific format groups. Fragment-based formats that lack an Fc part have limited half-life and cannot mediate Fc effector functions. IgG-like formats display only monovalent binding to each target.

In the field of cancer, the risk of many targeted therapies is that of the cancer adapting or mutating in a way that prevents that target from being functional. Further, the epitopes presented by one person may differ vastly compared with that of another person. Thus, there is an increasing need for off-the-shelf technologies that are readily adaptable to a particular situation and patient.

Accordingly, in some embodiments, the polypeptide may comprise an immune cell binding domain that binds to at least one immune cell receptor, optionally wherein the immune cell receptor is CD40, CLEC9A, DEC-205, XCR1 or TLR3. For example, the immune cell binding domain of a polypeptide of the present invention may bind to CD40.

In some embodiments, the polypeptide may be an antibody that is selected from ADC-1013; clones 1132/1133, 1140/1135, 1150/1151 and 1107/1108 from WO 2015/091853; CP-870,893, APX005M, ChiLob 7/4, and SEA-CD40.

Accordingly, the polypeptide may be an antibody that comprises or consists of any one or more of the following sequences:

```
Antibody 1132/1133
Variable heavy chain (VH) amino acid sequence:
                                           (SEQ ID NO: 1)
EVQLLESGGGLVQPGGSLRLSCAASGFTFSSYAMSWVRQAPGKGLEWVSG

IGSYGGGTYYADSVKGRFTISRDNSKNTLYLQMNSLRAEDTAVYYCARYV

NFGMDYWGQGTLVTVSS

Variable light chain (VL) amino acid sequence:
                                           (SEQ ID NO: 2)
DIQMTQSPSSLSASVGDRVTITCRASQSISSYLNWYQQKPGKAPKLLIYA

ASSLQSGVPSRFSGSGSGTDFTLTISSLQPEDFATYYCQQYGRNPPTFGQ

GTKLEIK

CDR amino acid sequences:
VH CDRs:
CDR1:
                                           (SEQ ID NO: 3)
GFTFSSYA

CDR2:
                                           (SEQ ID NO: 4)
IGSYGGGT

CDR3:
                                           (SEQ ID NO: 5)
ARYVNFGMDY

VL CDRs:
CDR1:
                                           (SEQ ID NO: 6)
QSISSY

CDR2:
                                           (SEQ ID NO: 7)
AAS

CDR3:
                                           (SEQ ID NO: 8)
QQYGRNPPT

Variable heavy chain (VH) nucleotide sequence:
                                           (SEQ ID NO: 9)
GAGGTGCAGCTGTTGGAGAGCGGGGGAGGCTTGGTACAGCCTGGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCAGGT

ATTGGTTCTTACGGTGGTGGTACATACTATGCAGACTCCGTGAAGGGCCG

GTTCACCATCTCCCGTGACAATTCCAAGAACACGCTGTATCTGCAAATGA

ACAGCCTGCGTGCCGAGGACACGGCTGTATATTATTGTGCGCGCTACGTT
```

```
AACTTCGGTATGGACTATTGGGGCCAGGGAACCCTGGTCACCGTCTCCTC
A
```

Variable light chain (VL) nucleotide sequence:
(SEQ ID NO: 10)
```
GACATCCAGATGACCCAGTCTCCATCCTCCCTGAGCGCATCTGTAGGAGA
CCGCGTCACCATCACTTGCCGGGCAAGTCAGAGCATTAGCAGCTATTTAA
ATTGGTATCAGCAGAAACCAGGGAAAGCCCCTAAGCTCCTGATCTATGCT
GCATCCAGTTTGCAAAGTGGGGTCCCATCACGTTTCAGTGGCAGTGGAAG
CGGGACAGATTTCACTCTCACCATCAGCAGTCTGCAACCTGAAGATTTTG
CAACTTATTACTGTCAACAGTACGGTCGTAACCCGCCCACTTTTGGCCAG
GGGACCAAGCTGGAGATCAAA
```

Antibody 1140/1135
Variable heavy chain (VH) amino acid sequence:
(SEQ ID NO: 11)
```
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARGP
VYSSVFDYWGQGTLVTVSS
```

Variable light chain (VL) amino acid sequence:
(SEQ ID NO: 12)
```
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPYTFGQ
GTKLEIK
```

CDR amino acid sequences:
VH CDRs:
CDR1:
(SEQ ID NO: 13)
GFTFSSYA

CDR2:
(SEQ ID NO: 14)
ISGSGGST

CDR3:
(SEQ ID NO: 15)
ARGPVYSSVFDY

VL CDRs:
CDR1:
(SEQ ID NO: 16)
QSISSY

CDR2:
(SEQ ID NO: 17)
AAS

CDR3:
(SEQ ID NO: 18)
QQSYSTPYT

Variable heavy chain (VH) nucleotide sequence:
(SEQ ID NO: 19)
```
GAGGTGCAGCTGTTGGAGAGCGGGGGAGGCTTGGTACAGCCTGGGGGGTC
CCTGCGCCTCTCCTGTGCAGCCAGCGGATTCACCTTTAGCAGCTATGCCA
TGAGCTGGGTCCGCCAGGCTCCAGGGAAGGGGCTGGAGTGGGTCTCAGCT
ATTAGTGGTAGTGGTGGTAGCACATACTATGCAGACTCCGTGAAGGGCCG
GTTCACCATCTCCCGTGACAATTCCAAGAACACGCTGTATCTGCAAATGA
ACAGCCTGCGTGCCGAGGACACGGCTGTATATTATTGTGCGCGCGGTCCG
GTTTACTCTTCTGTTTTTGACTATTGGGGCCAGGGAACCCTGGTCACCGT
CTCCTCA
```

Variable light chain (VL) nucleotide sequence:
(SEQ ID NO: 20)
```
GACATCCAGATGACCCAGTCTCCATCCTCCCTGAGCGCATCTGTAGGAGA
CCGCGTCACCATCACTTGCCGGGCAAGTCAGAGCATTAGCAGCTATTTAA
ATTGGTATCAGCAGAAACCAGGGAAAGCCCCTAAGCTCCTGATCTATGCT
GCATCCAGTTTGCAAAGTGGGGTCCCATCACGTTTCAGTGGCAGTGGAAG
CGGGACAGATTTCACTCTCACCATCAGCAGTCTGCAACCTGAAGATTTTG
CAACTTATTACTGTCAACAGAGTTACAGTACCCCTTATACTTTTGGCCAG
GGGACCAAGCTGGAGATCAAA
```

Antibody 1150/1151
Variable heavy chain (VH) amino acid sequence:
(SEQ ID NO: 21)
```
EVQLLESGGGLVQPGGSLRLSCAASGFTFSSYAMSWVRQAPGKGLEWVSG
IGGSSSYTSYADSVKGRFTISRDNSKNTLYLQMNSLRAEDTAVYYCARYY
SYHMDYWGQGTLVTVSS
```

Variable light chain (VL) amino acid sequence:
(SEQ ID NO: 22)
```
DIQMTQSPSSLSASVGDHVTITCRASQSISSYLNWYQQKPGKAPKLLIYA
ASSLQSGVPSRFSGSGSGTDFTLTISSLQPEDFATYYCQQYGSAPPTFGQ
GTKLEIK
```

CDR amino acid sequences
VH CDRs:
CDR1:
(SEQ ID NO: 23)
GFTFSSYA

CDR2:
(SEQ ID NO: 24)
IGGSSSYT

CDR3:
(SEQ ID NO: 25)
ARYYSYHMDY

VL CDRs:
CDR1:
(SEQ ID NO: 26)
QSISSY

CDR2:
(SEQ ID NO: 27)
AAS

CDR3:
(SEQ ID NO: 28)
QQYGSAPPT

Variable heavy chain (VH) nucleotide sequence:
(SEQ ID NO: 29)
```
GAGGTGCAGCTGTTGGAGAGCGGGGGAGGCTTGGTACAGCCTGGGGGGTC
CCTGCGCCTCTCCTGTGCAGCCAGCGGATTCACCTTTAGCAGCTATGCCA
TGAGCTGGGTCCGCCAGGCTCCAGGGAAGGGGCTGGAGTGGGTCTCAGGT
ATTGGTGGTTCTTCTTCTTACACATCTTATGCAGACTCCGTGAAGGGCCG
GTTCACCATCTCCCGTGACAATTCCAAGAACACGCTGTATCTGCAAATGA
ACAGCCTGCGTGCCGAGGACACGGCTGTATATTATTGTGCGCGCTACTAC
TCTTACCATATGGACTATTGGGGCCAGGGAACCCTGGTCACCGTCTCCTC
A
```

-continued

Variable light chain (VL) nucleotide sequence:
(SEQ ID NO: 30)
GACATCCAGATGACCCAGTCTCCATCCTCCCTGAGCGCATCTGTAGGAGA

CCACGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCACGTTTCAGTGGCAGTGGAAG

CGGGACAGATTTCACTCTCACCATCAGCAGTCTGCAACCTGAAGATTTTG

CAACTTATTACTGTCAACAGTACGGTTCTGCTCCGCCCACTTTTGGCCAG

GGGACCAAGCTGGAGATCAAA

Antibody 1107/1108
Variable heavy chain (VH) amino acid sequence:
(SEQ ID NO: 31)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCARRV

WGFDYWGQGTLVTVSS

Variable light chain (VL) amino acid sequence:
(SEQ ID NO: 32)
DIQMTQSPSSLSASVGDRVTITCRASQSISSYLNWYQQKPGKAPKLLIYA

ASSLQSGVPSRFSGSGSGTDFTLTISSLQPEDFATYYCQQYGVYPFTFGQ

GTKLEIK

CDR amino acid sequences:
VH CDRs:
CDR1:
(SEQ ID NO: 33)
GFTFSSYA

CDR2:
(SEQ ID NO: 34)
ISGSGGST

CDR3:
(SEQ ID NO: 35)
ARRVWGFDY

VL CDRs:
CDR1:
(SEQ ID NO: 36)
QSISSY

CDR2:
(SEQ ID NO: 37)
AAS

CDR3:
(SEQ ID NO: 38)
QQYGVYPFT

Variable heavy chain (VH) nucleotide sequence:
(SEQ ID NO: 39)
GAGGTGCAGCTGTTGGAGAGCGGGGGAGGCTTGGTACAGCCTGGGGGGTC

CCTGCGCCTCTCCTGTGCAGCCAGCGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTATGCAGACTCCGTGAAGGGCCG

GTTCACCATCTCCCGTGACAATTCCAAGAACACGCTGTATCTGCAAATGA

ACAGCCTGCGTGCCGAGGACACGGCTGTATATTATTGTGCGCGCCGTGTT

TGGGGTTTTGACTATTGGGGCCAGGGAACCCTGGTCACCGTCTCCTCAGG

Variable light chain (VL) nucleotide sequence:
(SEQ ID NO: 40)
GACATCCAGATGACCCAGTCTCCATCCTCCCTGAGCGCATCTGTAGGAGA

CCGCGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCACGTTTCAGTGGCAGTGGAAG

CGGGACAGATTTCACTCTCACCATCAGCAGTCTGCAACCTGAAGATTTTG

CAACTTATTACTGTCAACAGTACGGTGTTTACCCGTTCACTTTTGGCCAG

GGGACCAAGCTGGAGATCAAA

Antibody G12 (ADC-1013)
Variable heavy chain (VH) amino acid sequence:
(SEQ ID NO: 41)
EVQLLESGGGLVQPGGSLRLSCAASGFTFSTYGMHWVRQAPGKGLEWSY

ISGGSSYIFYADSVRGRFTISRDNSENALYLQMNSLRAEDTAVYYCARIL

RGGSGMDLWGQGTLVTVSS

Variable light chain (VL) amino acid sequence:
(SEQ ID NO: 42)
QSVLTQPPSASGTPGQRVTISCTGSSSNIGAGYNVYWYQQLPGTAPKLLI

YGNINRPSGVPDRFSGSKSGTSASLAISGLRSEDEADYYCAAWDKSISGL

VFGGGTKLTVLG

CDR amino acid sequences:
VH CDRs:
CDR1:
(SEQ ID NO: 43)
GFTFSTYGMH

CDR2:
(SEQ ID NO: 44)
GKGLEWLSYISGGSSYIFYADSVRGR

CDR3:
(SEQ ID NO: 45)
CARILRGGSGMDL

VL CDRs:
CDR1:
(SEQ ID NO: 46)
CTGSSSNIGAGYNVY

CDR2:
(SEQ ID NO: 47)
GNINRPS

CDR3:
(SEQ ID NO: 48)
CAAWDKSISGLV

Variable heavy chain (VH) nucleotide sequence:
(SEQ ID NO: 49)
GAGGTGCAGCTGTTGGAGTCTGGGGGAGGCTTGGTACAGCCTGGGGGGTC

CCTGAGACTCTCCTGTGCAGCCTCTGGATTCACCTTCAGTACTTATGGCA

TGCACTGGGTCCGCCAGGCTCCAGGGAAGGGGCTGGAGTGGCTTTCATAT

ATTAGTGGTGGTAGTAGTTACATTTTCTACGCAGACTCAGTGAGGGGCCG

ATTCACCATCTCCAGAGACAACTCCGAGAACGCGCTGTATCTGCAAATGA

ACAGCCTGAGAGCCGAGGACACGGCCGTGTATTACTGTGCGAGAATATTA

AGAGGCGGGAGCGGTATGGACCTCTGGGGCCAAGGTACACTGGTCACCGT

GAGCTCA

Variable light chain (VL) nucleotide sequence:
(SEQ ID NO: 50)
CAGTCTGTGCTGACTCAGCCACCCTCAGCGTCTGGGACCCCCGGGCAGAG

GGTCACCATCTCTTGCACTGGGAGCAGCTCCAACATCGGGGGGGGTTACA

ATGTATACTGGTATCAGCAGCTCCCAGGAACGGCCCCCAAACTCCTCATC

-continued

```
TATGGTAACATCAATCGGCCCTCAGGGGTCCCTGACCGATTCTCTGGCTC

CAAGTCTGGCACCTCAGCCTCCCTGGCCATCAGTGGGCTCCGGTCCGAGG

ATGAGGCTGATTATTACTGTGCAGCATGGGATAAGAGCATTTCTGGTCTG

GTTTTCGGCGGAGGAACCAAGCTGACGGTCCTAGGT
```

Accordingly, in some embodiments, the polypeptide comprising an immune cell binding domain and/or a tag binding domain, for example a peptide tag binding domain, is selected from the group consisting of: antibodies or antigen binding fragments thereof.

By "an antibody or an antigen-binding fragment thereof" we include substantially intact antibody molecules, as well as chimeric antibodies, humanised antibodies, isolated human antibodies, single chain antibodies, bispecific antibodies, antibody heavy chains, antibody light chains, homodimers and heterodimers of antibody heavy and/or light chains, and antigen-binding fragments and derivatives of the same. Suitable antigen-binding fragments and derivatives include Fv fragments (e.g. single chain Fv and disulphide-bonded Fv), Fab-like fragments (e.g. Fab fragments, Fab' fragments and F(ab)2 fragments), single variable domains (e.g. VH and VL domains) and single domain antibodies (dAbs, including single and dual formats [i.e. dAb-linker-dAb], and nanobodies). The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from E. coli, thus allowing the facile production of large amounts of the said fragments.

In one embodiment, the antigen-binding fragment is selected from the group consisting of: Fv fragments (such as a single chain Fv fragment, or a disulphide-bonded Fv fragment), Fab-like fragments (such as a Fab fragment; a Fab' fragment or a F(ab)2 fragment) and single domain antibodies.

The phrase "an antibody or an antigen-binding fragment thereof" is also intended to encompass antibody mimics (for example, non-antibody scaffold structures that have a high degree of stability yet allow variability to be introduced at certain positions). Those skilled in the art of biochemistry will be familiar with many such molecules, as discussed in Gebauer & Skerra, 2009 (the disclosures of which are incorporated herein by reference).

Exemplary antibody mimics include: affibodies (also called Trinectins; Nygren, 2008, FEBS J, 275, 2668-2676); CTLDs (also called Tetranectins; Innovations Pharmac. Technol. (2006), 27-30); adnectins (also called monobodies; Meth. Mol. Biol., 352 (2007), 95-109); anticalins (Drug Discovery Today (2005), 10, 23-33); DARPins (ankyrins; Nat. Biotechnol. (2004), 22, 575-582); avimers (Nat. Biotechnol. (2005), 23, 1556-1561); microbodies (FEBS J, (2007), 274, 86-95); peptide aptamers (Expert. Opin. Biol. Ther. (2005), 5, 783-797); Kunitz domains (J. Pharmacol. Exp. Ther. (2006) 318, 803-809); affilins (Trends. Biotechnol. (2005), 23, 514-522); affimers (Avacta Life Sciences, Wetherby, UK).

Also included within the scope of the invention are chimeric T cell receptors (also known as chimeric T cell receptors, chimeric immunoreceptors, and chimeric antigen receptors or CARs) (see Pule et al., 2003, the disclosures of which are incorporated herein by reference). These are engineered receptors, which graft an arbitrary specificity onto an immune effector cell. Typically, CARs are used to graft the specificity of a monoclonal antibody onto a T cell; with transfer of their coding sequence facilitated by retroviral vectors. The most common form of such molecules is fusions comprising a single-chain variable fragment (scFv) derived from a monoclonal antibody fused to CD3-zeta transmembrane and endodomain. When T cells express this fusion molecule, they recognize and kill target cells that express the transferred monoclonal antibody specificity.

Persons skilled in the art will further appreciate that the invention also encompasses modified versions of antibodies and antigen-binding fragments thereof, whether existing now or in the future, e.g. modified by the covalent attachment of polyethylene glycol or another suitable polymer (see below).

Methods of generating antibodies and antibody fragments are well known in the art. For example, antibodies may be generated via any one of several methods which employ induction of in vivo production of antibody molecules, screening of immunoglobulin libraries (Orlandi. et al, 1989; Winter et al., 1991, the disclosures of which are incorporated herein by reference) or generation of monoclonal antibody molecules by cell lines in culture. These include, but are not limited to, the hybridoma technique, the human B cell hybridoma technique, and the Epstein-Barr virus (EBV)-hybridoma technique (Kohler et al., 1975,Kozbor et al., 1985; Cote et al., 1983; Cole et al., 1984., the disclosures of which are incorporated herein by reference).

Suitable methods for the production of monoclonal antibodies are also disclosed in "Monoclonal Antibodies: A manual of techniques", H Zola (CRC Press, 1988, the disclosures of which are incorporated herein by reference) and in "Monoclonal Hybridoma Antibodies: Techniques and Applications", J G R Hurrell (CRC Press, 1982, the disclosures of which are incorporated herein by reference).

Likewise, antibody fragments can be obtained using methods well known in the art (see, for example, Harlow & Lane, 1988, "Antibodies: A Laboratory Manual", Cold Spring Harbor Laboratory, New York, the disclosures of which are incorporated herein by reference). For example, antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat or rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986, Riechmann et al., 1988, Presta, 1992, the disclosures of which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, Reichmann et al., 1988, Verhoeyen et al., 1988, U.S. Pat. No. 4,816,567, the disclosures of which are incorporated herein by reference) by substituting human complementarity determining regions with corresponding rodent complementarity determining regions. Accordingly, such humanised antibodies are chimeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, Marks et al., 1991, Cole et al., 1985, Boerner et al., 1991, the disclosures of which are incorporated herein by reference).

It will be appreciated by persons skilled in the art that the bispecific polypeptides, e.g. antibodies, of the present invention may be of any suitable structural format.

Accordingly, in some embodiments, the polypeptide is an antigen-binding fragment selected from the group consisting of: an Fv fragment (such as a single chain Fv fragment, or a disulphide-bonded Fv fragment); a Fab-like fragment (such as a Fab fragment; a Fab' fragment; or a F(ab)2 fragment); and domain antibodies.

In some embodiments, the tag binding domain, for example the peptide tag binding domain is an Fc region of an antibody or antibody fragment having the ability to specifically bind to the tag, for example to the peptide tag. For example, the tag, for example the peptide tag may be a molecule with affinity to the Fc portion of an antibody, such as an antibody or fragment thereof that is specific to Fc (an anti-Fc antibody or fragment thereof); and Protein A, which is a protein derived from Staphylococcus aureus that binds strongly to IgGs.

In one embodiment, the peptide tag is a 33 amino acid sequence as follows:

```
Z33:
                                        [SEQ ID NO: 51]
FNMQQQRRFYEALHDPNLNEEQRNAKIKSIRDD
```

Accordingly, in some embodiments the tag binding domain of the polypeptide of the invention is an Fc region of an antibody or antigen binding fragment thereof that is capable of binding to the Z33 peptide sequence of SEQ ID NO: 51.

In one embodiment, the peptide tag is linked to a larger peptide or polypeptide, for example that comprises an antigen or neoantigen, through a linker, for example a GSSSS linker [SEQ ID NO: 55] or a cleavable valine-citrulline linker.

Optionally, the binding domain localized to the Fc region can be engineered by introduction of mutations to enhance the affinity to the Fc-binding peptide tag. Such mutations would improve the stability of the DC-targeting antibody-neoantigen complex and prevent swapping of the Fc in an in vivo setting.

Also contemplated are embodiments wherein the polypeptide comprises at least 2 tag binding domains (for example at least 2 peptide tag binding domains), for example 3, 4, 5, 6 or more peptide tag binding domains (for example at least 3, 4, 5, 6 peptide tag binding domains). Where at least 2 tag binding domains are present, in some embodiments at least one is selected from the group consisting of: antibodies or antigen binding fragments thereof; and at least one may be an Fc region of an antibody having the ability to specifically bind to the peptide tag.

In one embodiment, the tag binding domain (for example the peptide tag binding domain) is a domain other than an Fc region. For instance, the polypeptide may comprise an Fc region, but the Fc region is not the domain that binds to the tagged antigen/neoantigen. In some embodiments the polypeptide may comprise a number of tag binding domains (for example a number of peptide tag binding domains) as described herein, and none of those are the Fc region, i.e. the Fc region is not used to bind to the tagged antigen/neoantigen.

In other embodiments, the Fc region is used to bind to the tagged antigen/neoantigen, or the Fc region is one of a number of binding domains used to bind to the tagged antigens.

Thus, a number of variations can be envisaged for the present invention, such as where the polypeptide comprises:

a) at least one immune cell binding domain that comprises or consists of an IgG antibody and at least one tag binding domain that comprises or consists of an IgG antibody;

b) at least one immune cell binding domain that comprises or consists of an IgG antibody and at least one tag binding domain that comprises or consists of an Fv fragment;

c) at least one immune cell binding domain that comprises or consists of an IgG antibody and at least one tag binding domain that comprises or consists of a Fab-like fragment;

d) at least one immune cell binding domain that comprises or consists of an IgG antibody and at least one tag binding domain that comprises or consists of a domain antibody;

e) at least one immune cell binding domain that comprises or consists of an IgG antibody and at least one tag binding domain that comprises or consists of a coiled-coil peptide tag;

f) at least one immune cell binding domain that comprises or consists of an Fv fragment and at least one tag binding domain that comprises or consists of an IgG antibody;

g) at least one immune cell binding domain that comprises or consists of a Fab-like fragment and at least one tag binding domain that comprises or consists of an IgG antibody;

h) at least one immune cell binding domain that comprises or consists of a domain antibody and at least one tag binding domain that comprises or consists of an IgG antibody;
i) at least one immune cell binding domain that comprises or consists of an IgG antibody and at least one tag binding domain that comprises or consists of an Fc region of an antibody having the ability to specifically bind to the tag;
j) at least one immune cell binding domain that comprises or consists of an Fv fragment and at least one tag binding domain that comprises or consists of an Fc region of an antibody having the ability to specifically bind to the tag;
k) at least one immune cell binding domain that comprises or consists of a Fab-like fragment and at least one tag binding domain that comprises or consists of an Fc region of an antibody having the ability to specifically bind to the tag;
l) at least one immune cell binding domain that comprises or consists of a domain antibody and at least one tag binding domain that comprises or consists of an Fc region of an antibody having the ability to specifically bind to the tag;
m) at least two immune cell binding domains that comprises or consists of an IgG antibody wherein the at least two dendritic cell binding domains bind to the same dendritic cell target, and at least one tag binding domain that comprises or consists of an Fc region of an antibody having the ability to specifically bind to the tag;
n) at least two immune cell binding domains that comprise or consist of an IgG antibody wherein the at least two dendritic cell binding domains bind to the same dendritic cell target, and at least one tag binding domain that comprises or consists of a coiled-coil peptide tag (such as E3 ((EIAALEK)×3)) that binds to a probe (such as K3 ((KIAALKE)×3) or K4 ((KIAALKE)×4)), wherein the probe is connected to the neoantigen,
optionally wherein the IgG antibody is an IgG1, IgG2, IgG3 or IgG4 antibody.

In some embodiments, the polypeptide is a bispecific polypeptide, and optionally comprises or consists of a format selected from the group consisting of (wherein the bispecific is comprised of binding domain 1 (B1) and binding domain 2 (B2):

a) IgG-scFv bispecific antibodies, optionally wherein B1 is an intact IgG and B2 is an scFv attached to B1 at the N-terminus of a light chain; at the C-terminus of a light chain; at the N-terminus of a heavy chain; and/or at the C-terminus of a heavy chain of the IgG. For example, the scFv could be attached to the N-terminus and C-terminus of the light chain; attached to the N-terminus of both the light and heavy chains, etc.
b) monovalent bispecific antibodies, such as a DuoBody® (Genmab AS, Copenhagen, Denmark) or 'knob-in-hole' bispecific antibody (for example, an scFv-KIH, scFv-KIHr, a BiTE-KIH or a BiTE-KIHr (see Xu et al., 2015, mAbs 7(1):231-242);
c) scFv2-Fc bispecific antibodies, (such as ADAPTIR™ bispecific antibodies from Emergent Biosolutions Inc);
d) BiTE/scFv2 bispecific antibodies;
e) DVD-Ig bispecific antibodies;
f) DART-based bispecific antibodies (for example, DART2-Fc or DART);
g) DNL-Fab3 bispecific antibodies; and
h) scFv-HSA-scFv bispecific antibodies
i) RUBY™ format antibodies, wherein the antibody comprises:
  (i) two copies of a first heavy chain polypeptide and two copies of a first light chain polypeptide, and
  (ii) two Fab fragments, the Fab fragments comprising a second heavy chain polypeptide and a second light chain polypeptide
  and wherein the first Fab fragment is fused to the C-terminus of the first copy of the first heavy chain polypeptide via the light chain polypeptide of the Fab fragment;
  and the second Fab fragment is fused to the C-terminus of the second copy of the first heavy chain polypeptide via the light chain polypeptide of the Fab fragment,
  and wherein
    a) the two copies of a first heavy chain polypeptide and two copies of a first light chain polypeptide form two immune cell binding domains and the two Fab fragments form a first and second tag binding domain; or
    b) the two copies of a first heavy chain polypeptide and two copies of a first light chain polypeptide form a first and a second tag binding domain, and the two Fab fragments form two immune cell binding domains.

For example, the bispecific antibody may be an IgG-scFv antibody. The IgG-scFv antibody may be in either VH-VL or VL-VH orientation. In one embodiment, the scFv may be stabilised by a S-S bridge between VH and VL.

In one embodiment, binding domain B1 and binding domain B2 are fused directly to each other.

In some embodiments, B1 is the immune cell binding domain and B2 is the tag binding domain. In other embodiments B1 is the tag binding domain and B2 is the immune cell binding domain.

In an alternative embodiment, binding domain B1 and binding domain B2 are joined via a polypeptide linker. For example, a polypeptide linker may be a short linker peptide between about 10 to about 25 amino acids. The linker is usually rich in glycine for flexibility, as well as serine or threonine for solubility, and can either connect the N-terminus of the VH with the C-terminus of the VL, or vice versa.

Thus, the linker may be selected from the group consisting of the amino acid sequence SGGGGSGGGGS [SEQ ID NO: 56], SGGGGSGGGGSAP [SEQ ID NO: 57], NFSQP [SEQ ID NO: 58], KRTVA [SEQ ID NO: 59], GGGSGGGG [SEQ ID NO: 60], GGGGSGGGGS [SEQ ID NO: 61], GGGGSGGGGSGGGGS [SEQ ID NO: 62], GST-SGSGKPGSGEGSTKG [SEQ ID NO: 63] (Whitlow et al. 1993), THTCPPCPEPKSSDK [SEQ ID NO: 64], GGGS [SEQ ID NO: 65], EAAKEAAKGGGGS [SEQ ID NO: 66], EAAKEAAK [SEQ ID NO: 67], or (SG)m, where m=1 to 7, for example m can be 1, 2, 3, 4, 5, 6 or 7.

In an alternative embodiment, the polypeptide comprises an Fc region or a variant of said region, optionally wherein the region is an IgG1, IgG2, IgG3 or IgG4 region, preferably IgG1 or IgG2.

In a further embodiment, the polypeptide is a monospecific antibody directed towards the immune cell target, and wherein the Fc region has been modified to be capable of binding to the tag, for example the peptide tag; or a bispecific antibody wherein one paratope comprises the immune cell binding domain and the second paratope comprises the tag binding domain (for example the tag binding domain), and optionally wherein the Fc region of the antibody has been modified to be capable of binding to the same or different tag, for example the same or different peptide tag.

It will be apparent that in addition to providing a polypeptide of the invention capable of targeting a peptide, such as an antigenic peptide or a neoantigen to a particular immune cell or population of immune cells, the invention also provides a complex comprising a polypeptide of the invention, as described herein, and a tagged antigen (for example a peptide tagged antigen), wherein the tagged antigen (for example the peptide tagged antigen) comprises the tag to which the tag binding domain of the polypeptide binds.

Preferences for features of the complex of the invention, for example in relation to the tagged antigens (for example tagged peptides that comprise the one or more antigens) and to the polypeptide of the invention are as described herein in relation to other aspects of the invention.

Accordingly, the complex of the invention comprises the polypeptide of the invention and the tagged antigen (for example a tagged peptide antigen). Preferences for the tag, along with the interaction between the tag and the polypeptide of the invention are as described herein in relation to other aspects of the invention. In addition, the tag (for example the peptide tag) may also be adapted to be multifunctional. For example, the tag may facilitate the binding of an antigen or epitope of interest to a polypeptide of the present invention, in addition to acting as an adjuvant. The term "adjuvant" means anything that can elicit or enhance an immune response, for example an immune response directed towards an antigen. Tags that also act as adjuvants may be tags that are epitopes for other immune cells, such as a T cell epitope or B cell epitope. A tag that comprises a sequence that is also a T cell epitope (which may be specific for CD4 or CD8 T cells) means that there may exist T cells in the subject that are specific to the sequence of the tag, and their interaction with said tag may boost or provoke their activity.

A B cell epitope means that the tag may have antibodies directed against it in situ. For example, a tag derived from the tetanus toxin (TTx), such as MTTE, is a B cell epitope that is widely spread within certain populations, i.e. a so-called universal B cell epitope. The term "universal" B cell epitope means that the majority of individuals in a given population have antibodies specific to that particular epitope. This may occur due to herd vaccination (i.e. the vaccination or the majority of a population against a particular disease, such as tetanus, measles, mumps, rubella etc).

Tags comprising particular universal B cell epitopes may be a detriment to the purpose of the present invention. For example, use of the MTTE peptide as a tag may be unworkable for large portions of the population due to patients having anti-MTTE antibodies. A polypeptide of the present invention that is specific to the MTTE peptide (being used as a tag attached to an antigen or epitope of interest) may have patient antibodies directed against it that prevent their intended function. Thus, polypeptides of the present invention are not intended to comprise a second binding domain specific for TTx or the MTTE peptide derived therefrom.

As stated above, in all embodiments the peptide tag is not a tetanus derived tag.

The suitability of a tag (for example a peptide tag) may be dependent on a number of factors. For example, a human peptide tag that is a natural human peptide is less likely to provoke an immune response against it (due to it not being considered "foreign" by the immune system). Alternatively, the tag (for example a peptide tag) could be derived from a non-human source, such as bacteria (i.e. a bacterial protein). The structure of the peptide tag is another consideration, such as the secondary and/or tertiary structures. Regarding secondary structures, it may be preferable that the peptide tag comprises largely of α-helices and few to no β-sheets. Thus, in a particular embodiment, a peptide tag may comprise or consist of an α-helical structure. Peptide secondary structure can be predicted using software that is publicly available, such as Jpred4 (http://www.compbio.dundee.ac.uk/jpred/, Drozdetskiy et al., Nucl. Acids Res. 43(W1): W389-W394, 2015) and PASTA 2.0 (http://protein.bio.uni-pd.it/pasta2/, Walsh et al., Nucl. Acids Res. 42(W): W301-W307, 2014), or can be determined experimentally using routine techniques such as circular dichroism spectroscopy (see e.g. Greenfield, N., Nat 5 Protoc. 1(6): 2876-2890, 2006).

In some embodiments the tag is a non-human tag, for example where the tag is a peptide tag, the peptide tag is a non-human peptide.

In one embodiment the complex of the invention comprises a polypeptide of the invention as described herein wherein the polypeptide of the invention comprises an Fc region, and a tagged antigen (for example a peptide tagged antigen), wherein the tag portion of the tagged antigen (for example a peptide tagged antigen) binds to the Fc region of the polypeptide of the invention. In one embodiment the tag has the sequence of [SEQ ID NO: 51] or a sequence with at least 80%, 85%, 90%, 95%, 98% or 100% sequence identity to SEQ ID NO: 51 and wherein the tag retains the ability to bind to the Fc region.

As stated above, the polypeptide of the invention may comprise more than one tag binding domain (for example more than one peptide tag binding domain), and may be capable of binding to more than one copy of the same tag, or to multiple different tags (for example multiple different peptide tags). Accordingly, in one embodiment the complex comprises a polypeptide of the invention, wherein the polypeptide comprises at least two tag binding domains (for example two peptide tag binding domains) capable of binding to at least two different tags (for example at least two different peptide tags), and wherein the complex comprises at least two tagged antigens (for example at least two peptide tagged antigens). The polypeptide may comprise at least 2, 3 or 4 tag binding domains (for example at least 2, 3 or 4 peptide tag binding domains), and the complex may comprise at least 2, 3 or 4 tagged antigens (for example peptide tagged antigens), for example tagged neoantigens.

Accordingly, a single complex may comprise multiple copies of a first tagged antigen, (for example a first peptide tagged antigen), for example a first tagged neoantigen; or may comprise at least 2, 3, or 4 different tagged antigens (for example may comprise at least 2, 3, or 4 different peptide tagged antigens), for example at least 2, 3 or 4 different tagged neoantigens or peptide tagged neoantigens.

The skilled person will understand what is meant by the term neoantigen, and we include the meaning of newly formed antigens that have not been previously recognized by the immune system in an individual. The genetic instability of tumor cells often leads to the occurrence of a large number of mutations, and expression of non-synonymous mutations can produce neoantigens, i.e. antigens that are specific to that tumor and to that individual. Neoantigens are highly immunogenic as they are not expressed in normal tissues. They can activate CD4+ and CD8+ T cells to generate an immune response and have the potential to become new targets of tumor immunotherapy. Neoantigens can arise from altered tumor proteins formed as a result of tumor mutations or from viral proteins.

We also include the meaning of antigens to which the individual has already been exposed, but which are more highly expressed by a tumour cell. In this case stimulation of the immune system by the polypeptide of the invention would be expected to raise an immune response that would be directed primarily to areas in which the antigen is most highly expressed—i.e. the tumour.

In preferred embodiments the antigen is a peptide, protein or fragment thereof that comprises an antigenic peptide or protein sequence.

Accordingly, it is considered to be advantageous if the complex of the invention comprises a neoantigen that has arisen in a particular tumour, since administration of the complex will result in the neoantigen being targeted to the desired immune cell, for example an APC such as a DC, where the immune cell can be activated, the neoantigen can be internalised and subsequently presented to other relevant cells of the immune system, ultimately directing the immune system against the tumour.

In one embodiment therefore the antigen is a neoantigen (for example a peptide neoantigen), and the complex of the invention comprises a polypeptide of the invention, and at least one tagged neoantigen such as at least one tagged peptide neoantigen. As discussed herein, it can be advantageous to administer multiple antigens, for example multiple neoantigens. In one embodiment the complex of the invention comprises a polypeptide of the invention and 2, 3, 4 or more different tagged antigens, for example peptide tagged antigens such as peptide tagged neoantigens. The peptide tagged neoantigens may be tagged with the same peptide tag, or the neoantigens may be tagged with different peptide antigens.

In particular embodiments, the antigen (for example the peptide tagged antigen) is a peptide that comprises an antigenic amino acid sequence that has been identified as a neoantigen that has arisen in a tumour or cell. The skilled person is readily able to sequence the genomic material of a given tumour to identify suitable neoantigens.

In some embodiments the tagged antigen, for example the peptide tagged antigen comprises an antigenic peptide that is a cancer antigen. The skilled person will appreciate which of the known cancer antigens it would be useful to target to immune cells, such as APC, for example DC. For example, in one embodiment the cancer antigen is an HPV-associated cancer antigen. In other embodiments, the neoantigen is a personalized neoantigen and requires the identification of suitable neoantigens in the individual tumour(s).

It will be clear to the skilled person that the polypeptide, complex and methods described herein are useful for targeting any antigenic peptide to immune cells, such as APC, for example DC. For example, the polypeptide, complex and methods described herein may be ultimately aimed at the treatment or prevention of cancer and may comprise cancer antigens or cancer neoantigens, as described herein. However, it will be clear that the present invention is also useful for the treatment or prevention of pathogenic infections, for example infection with a bacteria, fungus or virus. The skilled person will recognize that suitable antigens such as antigenic peptides from the pathogen should be tagged with the appropriate tag such as a peptide tag, to which the polypeptide of the invention binds. In this way, the necessary antigens are targeted to immune cells, such as APC, for example DC, initiating the appropriate immune response. Accordingly, in some embodiments the tagged antigen, for example the peptide tagged antigen is a peptide that comprises an antigenic amino acid sequence that is derived from a pathogen, for example wherein the pathogen is a bacteria, fungus or virus, for example wherein the virus is HPV.

The present invention also provides a method of forming the complex of the invention, wherein the complex is formed by contacting a polypeptide according to the invention (i.e. a polypeptide capable of binding to an immune cell and capable of binding to a tagged antigen, for example a peptide tagged antigen) with a tagged antigen (for example a peptide tagged antigen) in vitro, wherein the tagged antigen (for example peptide tagged antigen) comprises the corresponding tag (for example the peptide tag) to which the tag binding domain of the polypeptide binds. Preferences for features of the method of forming the complex of the invention, for example in relation to the tagged antigen(for example peptide tagged antigen) and to the polypeptide of the invention are as described herein in relation to other aspects of the invention.

The method can also be used to prepare a complex that comprises more than one antigen (for example more than one antigenic peptide) as will be apparent to the skilled person, for example by contacting the polypeptide of the invention with a number of tagged antigens. As discussed, the tagged antigens (for example peptide tagged antigens, i.e. antigens tagged with a peptide tag) may be tagged with the same tag, or with a different tag. The skilled person will understand that it is necessary that the polypeptide of the invention comprises the appropriate corresponding tag binding domain(s) so that the polypeptide can bind to the tag(s).

Where the polypeptide is to be bound to a number of different tagged antigens (whether the tags are the same or different), the contacting may be performed simultaneously, i.e. the polypeptide of the invention can be contacted to mixture of different tagged peptide antigens; or the contacting can be performed sequentially, wherein the polypeptide of the invention is contacted to a first tagged antigen (for example a first peptide tagged antigen), and is subsequently contacted to a second tagged antigen, and a third and fourth as appropriate (.e.g. a second, third and fourth peptide tagged antigen).

It will be clear to the skilled person that since the complex of the invention is considered to have therapeutic utility, the invention provides a pharmaceutical composition comprising a complex of the invention. Preferences for features of the pharmaceutical composition, for example in relation to the tagged antigen (for example peptide tagged antigen) and to the polypeptide of the invention are as described herein in relation to other aspects of the invention.

As will be apparent to the skilled person, the pharmaceutical composition will comprise the necessary excipients and carriers to ensure that the active agent, i.e. the complex, is maintained and supported and delivered in a functional state.

As discussed herein, in some situations it is considered advantageous if more than one antigen (for example more than one peptide tagged antigen, for example peptide tagged neoantigen), is administered to a patient. As described above, this could be achieved by preparing a complex wherein the polypeptide of the invention binds to a number of different antigens, for example a number of different peptide antigens or neoantigens—i.e. each individual complex of polypeptide/antigen comprises more than one antigen. However, an alternative means of delivering multiple antigens or neoantigens is to prepare a composition or pharmaceutical composition that comprises a number of different complexes of the invention, for example may comprise 1, 2, 3, 4, 5, 6, 7, 8, 9, 10 or more different complexes, wherein each complex is associated with a different peptide antigen or neoantigen, i.e. each individual complex only comprises one antigen, but the pharmaceutical composition comprises a number of different complexes.

Accordingly, in one embodiment, the invention provides a pharmaceutical composition wherein the composition comprises more than one different complex according to the invention, and wherein the sequence of the tagged antigens, for example tagged peptide antigen(s) of each complex are different, for example wherein the sequence of the tag is the same and the sequence of the peptide antigen is different; or wherein the sequence of the tag is different and the sequence of the peptide is different.

It will be clear that the complexes of the invention have advantageous therapeutic properties. Accordingly, the invention provides a number of medical uses relating to the administration of the complex or pharmaceutical composition of the invention. Preferences for features of the medical uses, for example in relation to the tagged peptide and to the polypeptide of the invention are as described herein in relation to other aspects of the invention.

The invention provides a complex of the invention, or a pharmaceutical composition of the invention, for use in medicine.

The invention also provides a method of treatment or method of preventing a disease, wherein the method comprises the administration of a complex of the invention, or a pharmaceutical composition of the invention.

The invention also provides the use of a complex of the invention, or a pharmaceutical composition of the invention for use in a method of manufacture of a medicament for the treatment or prevention of disease.

Therapeutic agents of the present invention are intended to be preformed as complexes, with the peptide tagged antigen, prior to administration. By preforming such complexes, it is considered to be more likely that the immune cell targeting portion of the complex will direct the antigen to the same immune cells. If the two (or more) components, wherein the first component is a polypeptide of the invention, i.e. comprising an immune cell specific domain and a tag binding domain (for example a peptide tag binding domain) and the second component is the tagged antigen (for example the peptide tagged antigen), were to be administered separately, they will traffic independently of each other and would need to essentially rely on chance events inside the body to bring the two in close proximity to allow complex formation For example, a peptide tagged antigen that is not bound to a polypeptide of the invention, i.e. with a domain specific to an immune cell target, such as a DC target (e.g. CD40), may fail to traffic to the DC and thus not be processed and presented to generate an adaptive immune response. Conversely, such a polypeptide (e.g. anti-CD40 polypeptide) that is not bound to the peptide tagged antigen provides no specific antigen to be processed and presented to generate an adaptive immune response, but may risk activating DC via CD40 against other epitopes they may present instead.

Thus, the present invention requires that the complexes are preformed prior to administration, to ensure the antigen or neoantigen reaches the intended cells based on the immune cell target of the polypeptide.

It will be clear to the skilled person that the complex and pharmaceutical compositions of the invention have a particular use in the treatment or prevention of cancer. In particular, where the peptide antigen is a neoantigen, identified from a patient's tumour, the complex and pharmaceutical composition are particularly useful in the treatment of cancer.

Accordingly, the invention provides a complex of the invention, or a pharmaceutical composition of the invention for use in a method of treating or preventing cancer, for example wherein the tagged antigen (for example the peptide tagged antigen) comprises an antigenic sequence that has been identified as a neoantigen that has arisen in a tumour or cell; or a cancer antigen.

The invention provides a method of treating or preventing cancer, wherein the method comprises administering a complex of the invention, or a pharmaceutical composition of the invention.

The invention also provides the use of a complex of the invention, or a pharmaceutical composition of the invention in the manufacture of a medicament for the treatment of cancer.

The polypeptide and complexes thereof may also be used as a therapeutic or prophylactic vaccine.

The invention also provides a complex of the invention, or a pharmaceutical composition of the invention for use in a method of treating or preventing a pathogenic infection, for example for treating or preventing a bacterial, fungal or viral infection, wherein the tagged peptide antigen comprises an antigenic sequence derived from a bacteria, fungus or virus, for example from HPV.

The invention provides a method of treating or preventing a pathogenic infection, for example for treating or preventing a bacterial, fungal or viral infection, wherein the method comprises administering a complex of the invention, or a pharmaceutical composition of the invention, wherein the tagged peptide antigen comprises an antigenic sequence derived from a bacteria, fungus or virus, for example from HPV.

The invention also provides the use of a complex of the invention, or a pharmaceutical composition of the invention in the manufacture of a medicament for the treatment or prevention of a pathogenic infection, for example for treating or preventing a bacterial, fungal or viral infection, wherein the tagged peptide antigen comprises an antigenic sequence derived from a bacteria, fungus or virus, for example from HPV.

The present invention lends itself to be used in methods of personalised therapy, particularly for the treatment of cancer. For example, a tissue sample from a tumour or other sample, for example a blood sample where the cancer is a blood cancer, or a sample of exosomes, can be analysed to identify neoantigens that have arisen specifically in the cancer cell or tissue, and not in other healthy tissues. Such analysis needs to be performed for each individual patient, producing a truly tailored therapy. Once these neoantigens have been identified, tagged versions of the antigens can easily be produced using, for example, standard laboratory cloning and expression techniques to create a peptide tagged antigen. Once the tagged antigens, for example peptide tagged antigens have been produced, they can be contacted with the or a polypeptide of the invention, producing one or more complexes that can be administered to the subject. It will be clear that the actual polypeptide of the invention, for use in the treatment of multiple patients, can be universal. The actual immune cell binding domains and tag binding domains (for example peptide tag binding domains) do not need to vary. The only variable part of the to system is the neoantigen sequence.

Accordingly, the invention provides a complex of the invention or a pharmaceutical composition of the invention for use in a method of personalised therapy, wherein a tumour-specific antigen such as a neoantigen or viral antigen have been identified as having arisen in a patient (i.e. is specific for the tumour, either by virtue of certain mutations occurring in the tumour DNA, or by virally transmitted antigens), and wherein the tagged antigenic peptide comprises the neoantigen.

In some embodiments the personalised therapy is for the treatment or prevention of cancer.

In some embodiments, the information regarding suitable neoantigens for use in the personalised treatment of a patient are already available. In other embodiments, the step of analysing the sample from the patient and obtaining the necessary information regarding suitable neoantigens is part of the method of the invention.

Accordingly, the invention provides a complex of the invention or a pharmaceutical composition of the invention for use in a method of personalised therapy, for example for the personalised treatment of cancer, wherein the method of personalised therapy involves the initial step of identifying a neoantigen that has arisen in a patient.

The invention also provides a method of personalised therapy, wherein the method comprises administering a complex of the invention or a pharmaceutical composition of the invention, for example for the personalised treatment of cancer. In some embodiments, the method involves the initial step of identifying a neoantigen that has arisen in a patient.

The invention provides the use of a complex of the invention or a pharmaceutical composition of the invention in the manufacture of a medicament for personalised therapy, for example for the personalised treatment of cancer. In some embodiments, the therapy involves the initial step of identifying a neoantigen that has arisen in a patient.

The invention also provides an in vitro method of producing a complex comprising a polypeptide of the invention and a tagged antigen (for example a peptide tagged antigen), wherein the tagged antigen (for example peptide tagged antigen) comprises the corresponding tag (for example peptide tag) to which the tag binding domain of the polypeptide binds, wherein the method comprises contacting the polypeptide of the invention with a tagged antigen (for example peptide tagged antigen) in vitro. Preferences for the in vitro method of producing a complex of the invention, for example in relation to the tagged peptide and to the polypeptide of the invention, are as described herein in relation to other aspects of the invention.

The complex of the invention is considered useful for in vivo administration. However, the complex of the invention is also useful in an in vitro or ex vivo method of activating an immune cell, wherein the method comprises contacting the immune cell with a complex of the invention or a pharmaceutical composition of the invention, wherein the immune cell comprises the immune cell target to which the immune cell binding domain of the polypeptide binds. Accordingly, the invention provides an in vitro or ex vivo method of activating an immune cell, wherein the method comprises contacting the immune cell with a complex of the invention or a pharmaceutical composition of the invention, wherein the immune cell comprises the immune cell target to which the immune cell binding domain of the polypeptide binds. Preferences for this in vitro or ex vivo method, such as the tagged peptide and the polypeptide of the invention are as described herein in relation to other aspects of the invention.

The invention also provides a nucleic acid encoding the polypeptide of the invention.

The invention provides a nucleic acid that encodes the polypeptide of the invention and which also encodes the tagged antigen of the invention.

The invention also provides a vector comprising the nucleic acid of the invention.

The invention also provides a vector comprising the nucleic acid that encodes the polypeptide of the invention and which also encodes the tagged antigen of the invention.

The invention provides a cell comprising the nucleic acid of the invention or the vector of the invention.

Preferences for the nucleic acids, vectors and cells of the invention are as described herein in relation to other aspects of the invention.

It will be clear to the skilled person that various embodiments of the invention lend themselves to being provided in kit form. For example, the invention provides a kit for the in vitro preparation of a complex according to the invention wherein the kit comprises one or more polypeptides of the invention and one or more tagged antigens, for example one or more peptide tagged antigens; and/or comprises one or more nucleic acids or vectors according to the invention. Preferences for features of the kits of the invention are as described herein in relation to other aspects of the invention.

In some embodiments, the kit comprises a buffer suitable for the in vitro formation of the complex.

The listing or discussion of an apparently prior-published document in this specification should not necessarily be taken as an acknowledgement that the document is part of the state of the art or is common general knowledge.

Preferences and options for a given aspect, feature or parameter of the invention should, unless the context indicates otherwise, be regarded as having been disclosed in combination with any and all preferences and options for all other aspects, features and parameters of the invention. For example, the invention provides a complex that comprises a polypeptide of the invention in RUBY™ format, that has 1 immune cell binding domain capable of binding to CD40 and one peptide tag binding domain that can bind to the FLAG tag, and wherein the complex comprises a peptide neoantigen identified in a patient, wherein the peptide neoantigen is tagged with a FLAG tag.

The invention also provides a complex formed by contacting a polypeptide of the invention that comprises a first and a second peptide tag binding domain, wherein the first and second peptide tag binding domain each binds to a different tag (i.e. a first and second tag), with a mixture of 2 peptide neoantigens, wherein one peptide neoantigen has been tagged with the first tag and the other peptide neoantigen has been tagged with the second tag.

FIGURE LEGENDS

FIG. 1: Human CD40 transgenic (hCD40tg) mice were given either anti-CD40-Fc(OVA) antibody or anti-CD40 antibody and the OVA peptide separately. Control mice received vehicle only. The treatments were given on two occasions, 7 days between. Seven days after the second treatment, inguinal lymph nodes were collected for flow cytometry analysis of viable CD45+ CD3+ CD8+ OVA-MHCI tetramer+ T cells. The graphs show frequency (±SEM) of OVA (SIINFEKL)-MHCI tetramer+ among CD8+ T cells.

Figure 2:
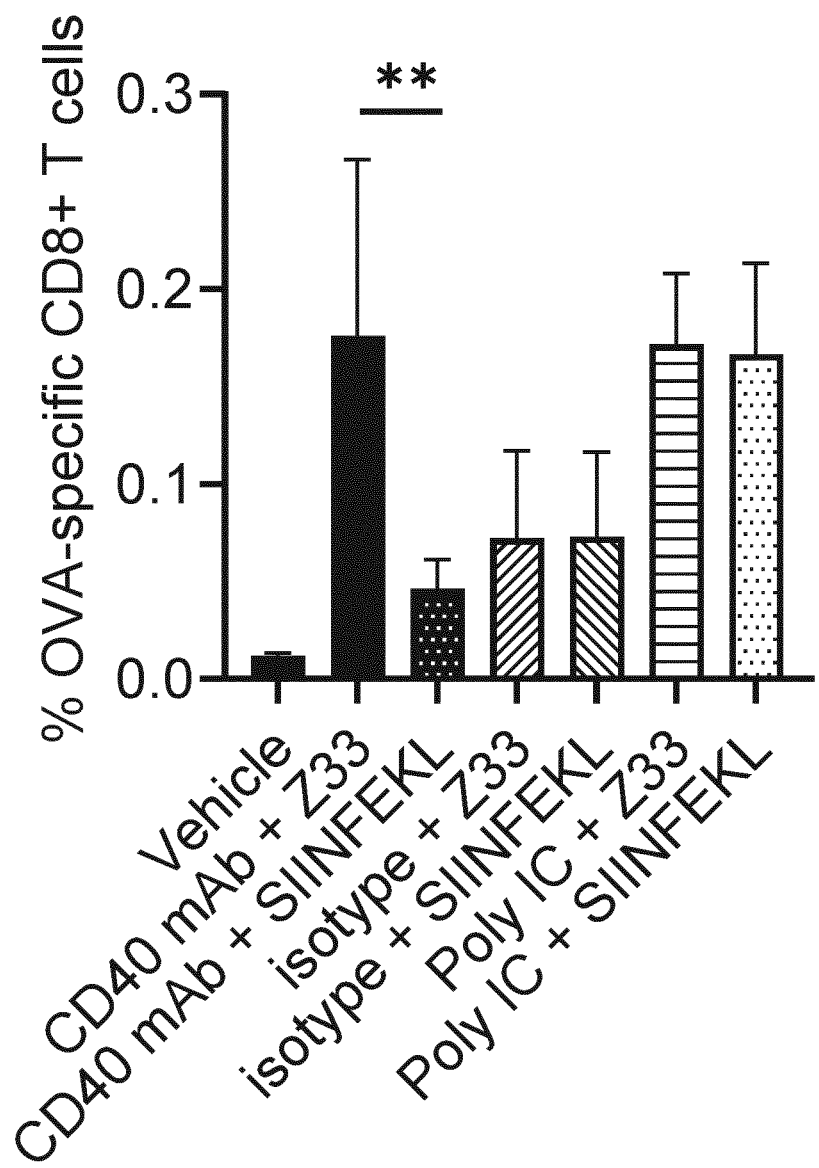

FIG. 2. Human CD40 transgenic (hCD40tg) mice were given OVA peptide-conjugated Fc-binding peptide (Z33) or free OVA peptide (SIINFEKL) in combination with anti-CD40 antibody, isotype control antibody, or Poly I:C adjuvant. Control mice received vehicle only. The treatments were given on two occasions, 7 days between. Seven days after the second treatment, inguinal lymph nodes were collected for flow cytometry analysis of viable CD45+

CD3+ CD8+ OVA-MHCI tetramer+ T cells. The graphs show frequency (±SEM) of OVA (SIINFEKL)-MHCI tetramer+ among CD8+ T cells.

Figure 3:
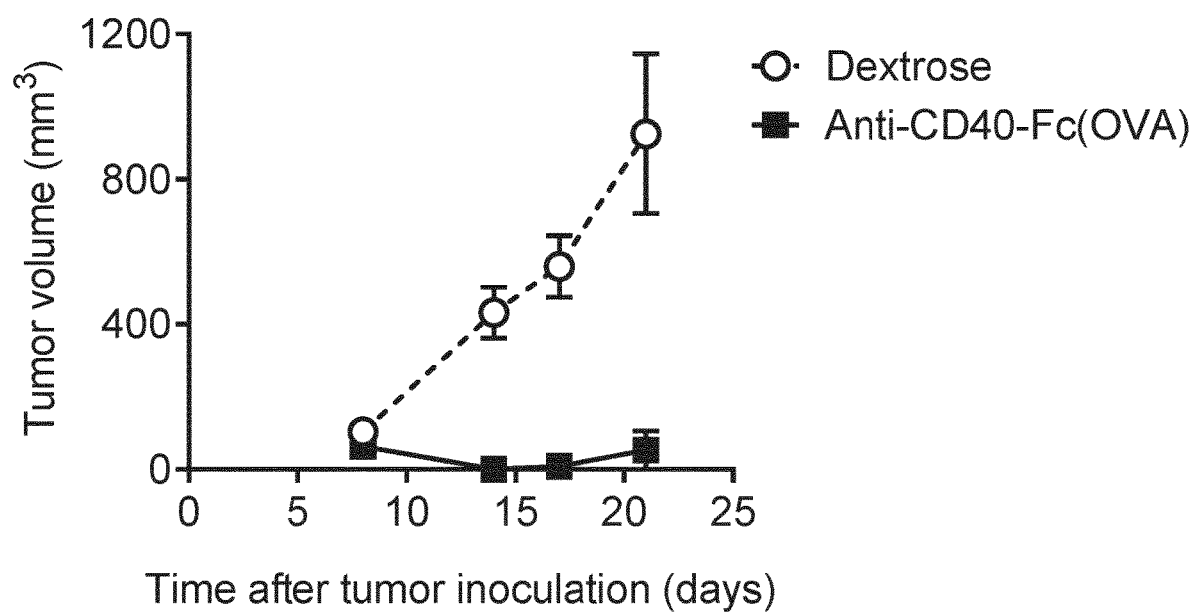

FIG. 3. Human CD40 transgenic (hCD40tg) mice were inoculated with EG7-OVA cells s.c. on the right flank on day 0, followed by s.c. treatment with either anti-CD40-Fc (OVA) antibody or vehicle control on the left flank on day 1 and 8. The graphs show the mean (±SEM) tumor volume.

Figure 4:
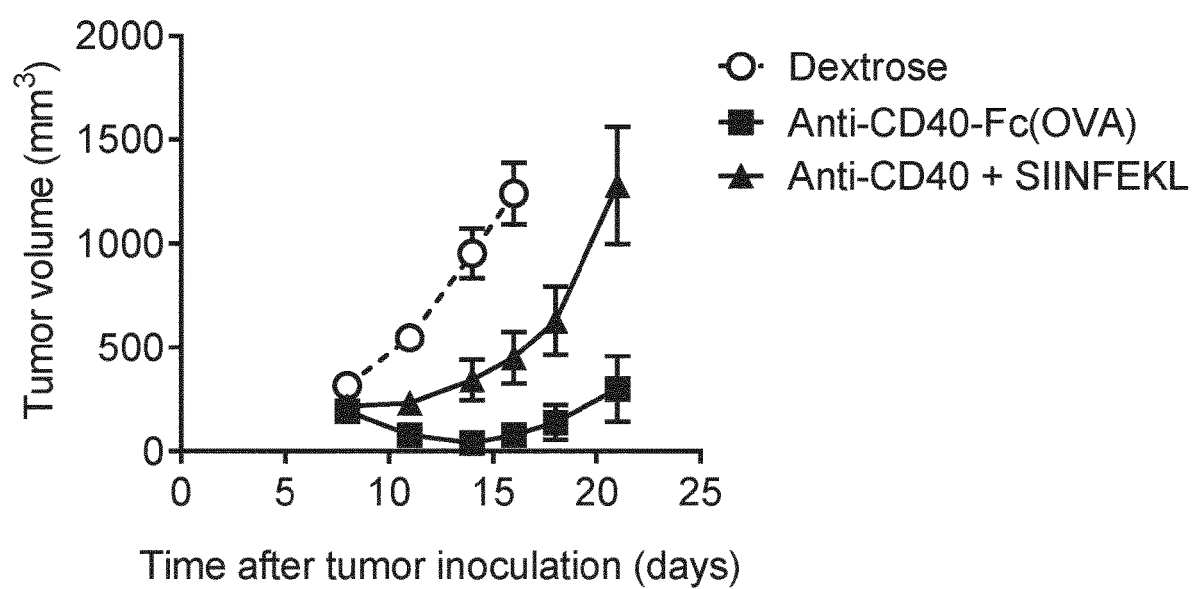

FIG. 4. Human CD40 transgenic (hCD40tg) mice were inoculated with EG7-OVA cells s.c. on the right flank on day 0, followed by s.c. treatment with anti-CD40-Fc(OVA) antibody, or anti-CD40 antibody and OVA peptide given separately, or vehicle control, on the left flank on day 1 and 8. The graphs show the mean (±SEM) tumor volume.

The invention is also defined by reference to the following numbered embodiment paragraphs:

1. A polypeptide comprising at least one immune cell binding domain and at least one tag binding domain,
   wherein the at least one immune cell binding domain is capable of specifically binding to an immune cell target; and
   wherein the at least one tag binding domain is capable of specifically binding to a peptide tag, wherein the peptide tag is not derived from tetanus toxin.

2. The polypeptide according to embodiment 1 wherein the polypeptide comprises more than one immune cell binding domain, optionally comprises 2, 3, or 4 immune cell binding domains.

3. The polypeptide according to any one of embodiments 1 or 2 wherein the polypeptide comprises more than one peptide tag binding domain, optionally comprises 2, 3, or 4 peptide tag binding domains.

4. The polypeptide according to embodiment 3 wherein each of the peptide tag binding domains binds to the same peptide tag.

5. The polypeptide according to embodiment 3 wherein one or more of the more than one peptide tag binding domains binds to a different peptide tag.

6. The polypeptide according to any one of embodiments 1-5 wherein the immune cell is an antigen presenting cell, such as a dendritic cell (DC), B cell and/or macrophage (preferably DC).

7. The polypeptide according to any one of embodiments 1-6 wherein the immune cell binding domain is an agonist of the immune cell target.

8. The polypeptide according to any one of embodiments 1-7 wherein the immune cell target is capable of mediating:
   activation of the immune cell; and/or
   internalisation of the polypeptide; and/or
   recruitment of conventional type I dendritic cells (cDC1).

9. The polypeptide according to any one of embodiments 1-8 wherein the immune cell binding domain binds to an immune cell receptor, optionally wherein the immune cell receptor is CD40, CLEC9A, DEC-205, XCR1 or TLR3.

10. The polypeptide according to embodiment 9 wherein the at least one immune cell binding domain binds to CD40.

11. The polypeptide according to any one of embodiments 1-10 wherein the immune cell binding domain is an antibody selected from: ADC-1013; clones 1132/1133, 1140/1135, 1150/1151 and 1107/1108 from WO 2015/091853; CP-870, 893, APX005M, ChiLob 7/4, SEA-CD40;
   wherein:
   ADC-1013 comprises one or more sequences selected from SEQ ID NO: 41-48;
   1132/1133 comprises one or more sequences selected from SEQ ID NO: 1-8;
   1140/1135 comprises one or more sequences selected from SEQ ID NO: 11-18;
   1150/1151 comprises one or more sequences selected from SEQ ID NO: 21-28;
   1107/1108 comprises one or more sequences selected from SEQ ID NO: 31-38.

12. The polypeptide according to any one of embodiments 1-11 wherein the peptide tag binding domain is capable of binding to a FLAG tag (DYKDDDDK) or a peptide probe sequence, optionally wherein the peptide probe sequence is a coiled-coil peptide tag E3 comprising the amino acid sequence (EIAALEK)×3.

13. The polypeptide according to any one of embodiments 1-12 wherein the peptide tag is a non-human peptide.

14. The polypeptide according to any one of embodiments 1-13 wherein the immune cell binding domain is selected from the group consisting of: antibodies or antigen binding fragments thereof.

15. The polypeptide according to any one of embodiments 1-14 wherein the peptide tag binding domain is:
   a) selected from group consisting of: antibodies or antigen binding fragments thereof; and/or
   b) is not an Fc region.

16. The polypeptide according to any one of embodiments 14 or 15 wherein the antigen-binding fragment is selected from the group consisting of: an Fv fragment (such as a single chain Fv fragment, or a disulphide-bonded Fv fragment); a Fab-like fragment (such as a Fab fragment; a Fab' fragment; or a F(ab)2 fragment); and domain antibodies.

17. The polypeptide according to any one of embodiments 1-14 and 16 wherein the peptide tag binding domain is an Fc region of an antibody having the ability to specifically bind to the peptide tag.

18. The polypeptide according to any one of embodiments 1-17 wherein the polypeptide comprises at least 2 peptide tag binding domains, wherein at least one peptide tag binding domain is selected from the group consisting of: antibodies or antigen binding fragments thereof; and wherein at least one peptide tag binding domain is an Fc region of an antibody having the ability to specifically bind to the peptide tag.

19. The polypeptide according to any one of embodiments 1-18 wherein the polypeptide comprises:
   a) at least one immune cell binding domain that comprises or consists of an IgG antibody and at least one peptide tag binding domain that comprises or consists of an IgG antibody;
   b) at least one immune cell binding domain that comprises or consists of an IgG antibody and at least one peptide tag binding domain that comprises or consists of an Fv fragment;
   c) at least one immune cell binding domain that comprises or consists of an IgG antibody and at least one peptide tag binding domain that comprises or consists of a Fab-like fragment;
   d) at least one immune cell binding domain that comprises or consists of an IgG antibody and at least one peptide tag binding domain that comprises or consists of a domain antibody;
   e) at least one immune cell binding domain that comprises or consists of an IgG antibody and at least one peptide tag binding domain that comprises or consists of a coiled-coil peptide tag (such as E3 ((EIAALEK)×3)) that binds to a probe (such as K3 ((KIAALKE)×3) or K4 ((KIAALKE)×4), wherein the probe is connected to the neoantigen;

f) at least one immune cell binding domain that comprises or consists of an Fv fragment and at least one peptide tag binding domain that comprises or consists of an IgG antibody;

g) at least one immune cell binding domain that comprises or consists of a Fab-like fragment and at least one peptide tag binding domain that comprises or consists of an IgG antibody;

h) at least one immune cell binding domain that comprises or consists of a domain antibody and at least one peptide tag binding domain that comprises or consists of an IgG antibody;

i) at least one immune cell binding domain that comprises or consists of an IgG antibody and at least one peptide tag binding domain that comprises or consists of an Fc region of an antibody having the ability to specifically bind to the peptide tag;

j) at least one immune cell binding domain that comprises or consists of an Fv fragment and at least one peptide tag binding domain that comprises or consists of an Fc region of an antibody having the ability to specifically bind to the peptide tag;

k) at least one immune cell binding domain that comprises or consists of a Fab-like fragment and at least one peptide tag binding domain that comprises or consists of an Fc region of an antibody having the ability to specifically bind to the peptide tag;

l) at least one immune cell binding domain that comprises or consists of a domain antibody and at least one peptide tag binding domain that comprises or consists of an Fc region of an antibody having the ability to specifically bind to the peptide tag;

m) at least two immune cell binding domains that comprise or consist of an IgG antibody wherein the at least two dendritic cell binding domains bind to the same dendritic cell target, and at least one peptide tag binding domain that comprises or consists of an Fc region of an antibody having the ability to specifically bind to the peptide tag;

n) at least two immune cell binding domains that comprise or consist of an IgG antibody wherein the at least two dendritic cell binding domains bind to the same dendritic cell target, and at least one peptide tag binding domain that comprises or consists of a coiled-coil peptide tag (such as E3 ((EIAALEK)×3)) that binds to a probe (such as K3 ((KIAALKE)×3) or K4 ((KIAALKE)×4), wherein the probe is connected to the neoantigen, optionally wherein the IgG antibody is an IgG1, IgG2, IgG3 or IgG4 antibody.

20. The polypeptide according any one of embodiments 1-19 wherein the polypeptide is a bispecific polypeptide, and optionally comprises or consists of a format selected from the group consisting of:
a) IgG-scFv bispecific antibodies;
b) monovalent bispecific antibodies;
c) scFv2-Fc bispecific antibodies;
d) BiTE/scFv2 bispecific antibodies;
e) DVD-Ig bispecific antibodies;
f) DART-based bispecific antibodies;
g) DNL-Fab3 bispecific antibodies; and
h) scFv-HSA-scFv bispecific antibodies
i) RUBY™ format antibodies, wherein the antibody comprises:
   (i) two copies of a first heavy chain polypeptide and two copies of a first light chain polypeptide, and
   (ii) two Fab fragments, the Fab fragments comprising a second heavy chain polypeptide and a second light chain polypeptide
   and wherein the first Fab fragment is fused to the C-terminus of the first copy of the first heavy chain polypeptide via the light chain polypeptide of the Fab fragment;
   and the second Fab fragment is fused to the C-terminus of the second copy of the first heavy chain polypeptide via the light chain polypeptide of the Fab fragment,
   and wherein
      a) the two copies of a first heavy chain polypeptide and two copies of a first light chain polypeptide form two immune cell binding domains and the two Fab fragments form a first and second tag binding domain; or
      b) the two copies of a first heavy chain polypeptide and two copies of a first light chain polypeptide form a first and a second tag binding domain, and the two Fab fragments form two immune cell binding domains.

21. The polypeptide according to any one of embodiments 1-20 wherein the polypeptide comprises an Fc region or a variant of said region, optionally wherein the region is an IgG1, IgG2, IgG3 or IgG4 region, optionally IgG1 or IgG2.

22. The polypeptide according to any of embodiments 1-21 wherein the polypeptide is
a monospecific antibody directed towards the immune cell target, and wherein the Fc region has been modified to be capable of binding to the peptide tag;
a bispecific antibody wherein one paratope comprises the immune cell binding domain and the second paratope comprises the peptide tag binding domain, and optionally wherein the Fc region of the antibody has been modified to be capable of binding to a peptide tag.

23. A complex comprising a polypeptide according to any one of embodiments 1-22 and a tagged peptide antigen, wherein the tagged peptide antigen comprises the peptide tag to which the tag binding domain of the polypeptide binds.

24. The complex of embodiment 23 wherein the polypeptide comprises at least two peptide tag binding domains capable of binding to at least two different peptide tags, and wherein the complex comprises at least two tagged peptide antigens.

25. The complex according to any one of embodiments 23 or 24 wherein the tagged peptide antigen comprises an antigenic sequence that has been identified as a neoantigen that has arisen in a tumour or cell.

26. The complex according to any one of embodiments 23 and 24 wherein the tagged peptide antigen comprises an antigenic peptide sequence that is a cancer antigen, optionally wherein the cancer antigen is a Human Papillomavirus (HPV)-associated cancer antigen.

27. The complex according to any one of embodiments 23 or 24 wherein the tagged peptide antigen comprises an antigenic sequence that is derived from a pathogen, optionally wherein the pathogen is a bacteria, fungus or virus, optionally wherein the virus is Human Papillomavirus (HPV).

28. A complex formed by contacting a polypeptide according to any of embodiments 1-22 with a tagged peptide antigen in vitro, wherein the tagged peptide antigen comprises the peptide tag to which the tag binding domain of the polypeptide binds.

29. A pharmaceutical composition comprising a complex according to any of embodiments 23 and 28.

30. The pharmaceutical composition according to embodiment 29 wherein the composition comprises more than one different complex according to any of embodiments 23-28, and wherein the sequence of the tagged peptide antigen(s) of each complex are different, optionally wherein the sequence of the tag is the same and the sequence of the peptide antigen is different; or wherein the sequence of the tag is different and the sequence of the peptide is different.

31. A complex according to any one of embodiments 23-28 or a pharmaceutical composition according to any one of embodiments 29 or 30 for use in medicine.

32. A complex according to any one of embodiments 23-28 or a pharmaceutical composition according to any one of embodiments 29 or 30 for use in a method of treating or preventing cancer, optionally wherein the tagged peptide antigen comprises an antigenic sequence that has been identified as a neoantigen that has arisen in a tumour or cell; or a cancer antigen.

33. A complex according to any one of embodiments 23-28 or a pharmaceutical composition according to any one of embodiments 29 or 30 for use in a method of treating or preventing a pathogenic infection,
optionally for treating or preventing a bacterial, fungal or viral infection, wherein the tagged peptide antigen comprises an antigenic sequence derived from a bacteria, fungus or virus, optionally from Human Papillomavirus (HPV).

34. A complex according to any one of embodiments 23-28 or a pharmaceutical composition according to any one of embodiments 29 or 30 for use in a method of personalised therapy, wherein a neoantigen has been identified as having arisen in a patient, and wherein the tagged antigenic peptide comprises the neoantigen.

35. The complex for use according to embodiment 34 wherein the personalised therapy is for the treatment or prevention of cancer.

36. The complex for use according to any of embodiments 34 or 35 wherein the method of personalised therapy involves the initial step of identifying a neoantigen that has arisen in a patient.

37. A method for the treatment or prevention of a disease wherein the method comprises administering a complex according to any one of embodiments 23-28 or a pharmaceutical composition according to any one of embodiments 29 or 30.

38. A method for the treatment or prevention of cancer, wherein the method comprises administering a complex according to any one of embodiments 23-28 or a pharmaceutical composition according to any one of embodiments 29 or 30,
optionally wherein the tagged peptide antigen comprises an antigenic sequence that has been identified as a neoantigen that has arisen in a cell, optionally a tumour cell; or a cancer antigen.

39. A method for the treatment or prevention of a pathogenic infection, wherein the method comprises administering a complex according to any one of embodiments 23-28 or a pharmaceutical composition according to any one of embodiments 29 or 30,
optionally wherein the method is for the treatment of prevention of a bacterial, fungal or viral infection, wherein the tagged peptide antigen comprises an antigenic sequence derived from a bacteria, fungus or virus, optionally from Human Papillomavirus (HPV).

40. A method for the personalised treatment or prevention of a disease in a patient, wherein the method comprises administering a complex according to any one of embodiments 23-28 or a pharmaceutical composition according to any one of embodiments 29 or 30,
optionally wherein the tagged peptide antigen comprises an antigenic sequence that has been identified as a neoantigen that has arisen in a cell, optionally a tumour cell; or a cancer antigen.

41. A method for personalised therapy, comprising administering a complex according to any of embodiments 23-28 or a pharmaceutical composition according to any of embodiments 29 or 30 to a patient, wherein a neoantigen has been identified as having arisen in the patient, and wherein the tagged antigenic peptide comprises the neoantigen.

42. The method according to embodiment 41 wherein the personalised therapy is for the treatment or prevention of cancer.

43. The method according to any one of embodiments 41 or 42 wherein the method of personalised therapy involves the initial step of identifying a neoantigen that has arisen in a patient.

44. A method of producing a complex comprising a polypeptide according to any one of embodiments 1-22 and a tagged peptide antigen, wherein the tagged peptide antigen comprises the peptide tag to which the tag binding domain of the polypeptide binds, wherein the method comprises contacting the polypeptide according to any of embodiments 1-22 with a tagged peptide antigen in vitro.

45. An in vitro or ex vivo method of activating an immune cell, wherein the method comprises contacting the immune cell with a complex according to any of embodiments 23-28 or a pharmaceutical composition according to any of embodiments 29 or 30, wherein the immune cell comprises the immune cell target to which the immune cell binding domain of the polypeptide binds.

46. A nucleic acid encoding the polypeptide according to any of embodiments 1-22.

47. A vector comprising the nucleic acid according to embodiment 46.

48. A cell comprising the nucleic acid according to embodiment 46 or the vector according to embodiment 47.

49. A kit for the in vitro preparation of a complex according to any of embodiments 23-28 wherein the kit comprises a polypeptide according to any of embodiments 1-22 and a tagged peptide antigen.

50. The kit according to embodiment 49 wherein the kit comprises a buffer suitable for the in vitro formation of the complex.

Features of the invention are as illustrated below in the following Examples.

Example 1: Priming of Ovalbumin-specific CD8+ T Cells by Anti-CD40-Fc(OVA) Antibody Background and Aim The OVA peptide SIINFEKL [SEQ ID NO: 70] was conjugated to the Fc of an anti-CD40 antibody (bivalent, monospecific) by use of Z33, a 33 amino acid long Fc-binding peptide, which binds between the CH2 and CH3 region of the Fc domain. The SIINFEKL peptide was in turn covalently linked to the Z33 peptide via a GSSSS linker. The purpose with this anti-CD40-Fc(OVA) antibody is to evaluate a concept wherein a peptide is conjugated to an anti-CD40 agonist and how such conjugation impacts T cell responses to the peptide. Ultimately, the OVA peptide can be exchanged to one or more tumor antigens to induce an immune response directed against tumor cells expressing such antigen(s).

Thus, the aim of this experiment was to evaluate the effect of the anti-CD40-Fc(OVA) antibody on the priming of OVA-specific CD8+ T cells, compared to an anti-CD40 antibody and OVA peptide administered separately.

Materials and Methods

Human CD40 transgenic (hCD40tg) mice, 8-9 weeks of age, were given a mixture of 33 μg anti-CD40 antibody and 18.9 μg Z33-OVA complex s.c. on two occasions, 7 days between. Additional cohorts of mice were instead given 33 μg anti-CD40 antibody and 3.3 μg OVA peptide separately or vehicle (PBS) control.

Seven days after the second treatment, mice were sacrificed and inguinal lymph nodes collected. The lymph nodes were mashed through cell strainers to obtain single cell suspensions and the cells were subsequently Fc blocked and stained with an antibody cocktail containing fluorescently-labelled anti-mouse antibodies for CD11b, CD19, MHCII, NK1.1 (dump channel), and CD45, CD3, CD4 and CD8, as well as OVA (SIINFEKL) MHCI tetramer. The cells were also stained with Fixable Viability Stain 780 (BD Biosciences) to assess the cell viability. Samples were analysed by flow cytometry in order to determine the frequency of viable CD45+ CD3+ CD8+ OVA-MHCI tetramer+ T cells.

Results and Conclusions

The data (shown in FIG. 1) demonstrate that treatment with anti-CD40-Fc(OVA) antibody results in a superior expansion of OVA-specific CD8+ T cells, compared to treatment with anti-CD40 antibody and OVA peptide separately. These data thus support that conjugation of an OVA peptide to an anti-CD40 antibody, results in more potent T cell priming compared to when the antibody and the peptide are administered separately.

Example 2: Effect on Priming of OVA-specific T Cells in Vivo

Background and Aim

The OVA peptide-linked Fc-binding peptide Z33 is capable of binding to antibodies, thereby forming an antibody-antigenic peptide complex. By using Z33-OVA in combination with a CD40 agonistic antibody, the antigenic peptide is targeted to CD40-expressing antigen-presenting cells such as dendritic cells (DC), which enhances cross-presentation of the antigen and increases priming of antigen-specific T cells. The purpose with this Fc-binding peptide is to generate a concept where T cell priming is improved when the Fc-binding peptide is combined with a DC-targeting and activating antibody. The aim of this experiment was to evaluate the effect on T cell priming when Z33-OVA or free OVA peptide is combined with either a CD40 agonistic antibody, an isotype control antibody, or an adjuvant to which Z33 does not bind.

Materials and Methods

Human CD40 transgenic (hCD40tg) mice, 12-14 weeks of age, were given a mixture of 18.9 μg Z33-OVA peptide or a molar equivalent dose of 3.3 μg free OVA peptide (SIINFEKL) and either 33 μg anti-CD40 antibody, 33 μg isotype control antibody, or 50 μg Poly I:C (a TLR3 ligand used as adjuvant) s.c. on two occasions, 7 days between. An additional cohort of mice were instead given vehicle (PBS) control.

Seven days after the second treatment, mice were sacrificed and inguinal lymph nodes collected. The lymph nodes were mashed through cell strainers to obtain single cell suspensions and the cells were subsequently Fc blocked and stained with an antibody cocktail containing fluorescently-labelled anti-mouse antibodies for CD11 b, CD19, MHCII, NK1.1 (dump channel), and CD45, CD3, CD4 and CD8, as well as OVA (SIINFEKL) MHCI tetramer. The cells were also stained with Fixable Viability Stain 780 (BD Biosciences) to assess the cell viability. Samples were analysed by flow cytometry in order to determine the frequency of viable CD45+ CD3+ CD8+ OVA-MHCI tetramer+ T cells.

Results and Conclusions

The data (shown in FIG. 2) demonstrate that when Z33-OVA or OVA peptide were combined with anti-CD40 antibody, Z33-OVA induced superior expansion of OVA-specific CD8+ T cells. In contrast, Z33-OVA and OVA peptide induced similar levels of OVA-specific CD8+ T cell expansion when combined with isotype control antibody or Poly I:C adjuvant. These data thus support that the DC-targeting and/or agonistic properties of the OVA-conjugated antibody are important for achieving a more potent T cell priming compared to separate administration of peptide and antibody. Further, an immunostimulatory signal alone was not sufficient to induce superior T cell expansion with Z33-OVA compared to OVA peptide, further supporting the notion that conjugating the antigenic peptide to a DC-targeting agonistic antibody is important for achieving an improved T cell priming effect.

Example 3: Anti-tumor Efficacy of an OVA-expressing Tumor Model, Comparing Anti-CD40-Fc(OVA) to Vehicle Control Background and Aim By treating mice subcutaneously with the anti-CD40-Fc(OVA) antibody (i.e. anti-CD40 antibody complexed with the Z33-OVA peptide), an OVA-specific T cell response was induced in draining lymph nodes. Ultimately, the OVA peptide can be exchanged for tumor antigen peptides to induce a tumor-specific immune response against tumors expressing such antigens. This tumor-targeting immune response would be expected to reduce the growth of an established tumor.

Thus, the aim of this experiment was to evaluate the effect of the anti-CD40-Fc(OVA) antibody on the growth of the OVA-expressing tumor EG7-OVA in a therapeutic vaccination setting.

Materials and Methods

Human CD40 transgenic (hCD40tg) female mice, 10-12 weeks of age, were inoculated with $1.0 \times 10^6$ EG7-OVA cells s.c. on the right flank on day 0. On day 1 and 8, mice were given either a mixture of 100 μg anti-CD40 antibody and 57 μg Z33-OVA peptide (anti-CD40-Fc(OVA) antibody) (which were mixed together prior to administration to allow complexes between the antibody and tagged antigen to form prior to administration to the mice) or vehicle control (Dextrose) s.c. on the left flank. Tumor volume and survival was monitored.

Results and Conclusions

The data (shown in FIG. 3) demonstrate that treatment with anti-CD40-Fc(OVA) antibody results in a significantly reduced tumor volume (p=0.0022 on day 14, 17 and 21) compared to vehicle control. These data indicate that the potent T cell priming induced by treatment with anti-CD40-conjugated OVA peptide is associated with an anti-tumor effect resulting in delayed growth of an OVA-expressing tumor.

Example 4: Comparison of the Anti-tumor Efficacy of CD40-Fc(OVA) (Pre-mixed Combination of Anti-CD40 and Z33-OVA) and Separate Administration of Anti-CD40 and OVA in an OVA-expressing Tumor Model Background and Aim Treatment with anti-CD40-Fc(OVA) antibody was shown to result in a significantly reduced tumor volume (p=0.0022 on day 14, 17 and 21) compared to vehicle control (Example 3).

The aim of this experiment was to evaluate the effect of the anti-CD40-Fc(OVA) antibody (i.e. the pre-mixed complex of the anti-CD40 antibody and the Z33-OVA peptide) on the growth of the OVA-expressing tumor EG7-OVA in a therapeutic vaccination setting, compared to the separate administration of the anti-CD40 and OVA peptide (SIINFEKL).

Materials and Methods

Human CD40 transgenic (hCD40tg) female mice, 9-11 weeks of age, were inoculated with $1.0 \times 10^6$ EG7-OVA cells s.c. on the right flank on day 0. On day 1 and 8, mice were given either a mixture of 100 μg anti-CD40 antibody and 19 μg Z33-OVA peptide (anti-CD40-Fc(OVA) antibody) (which were mixed together prior to administration to allow complexes between the antibody and tagged antigen to form prior to administration to the mice) or anti-CD40 and 3.3 μg OVA peptide (a molar equivalent dose to Z33-OVA peptide) s.c. on the left flank. Tumor volume and survival was monitored.

Results and Conclusions

The data (shown in FIG. 4) demonstrates that treatment with anti-CD40-Fc(OVA) antibody results in a significantly reduced tumor volume (p=0.0132 on day 11; p=0.0061 on day 14; p=0.0349 on day 16; p=0.0278 on day 18; p=0.0056 on day 21) compared to separate administration of the anti-CD40 antibody and OVA peptide (SIINFEKL). These data indicate that targeting the OVA peptide to the dendritic cells through the formation of a complex with the anti-CD40 antibody has a significantly enhanced effect on the reduction of tumor growth compared to administration of the OVA peptide in a non-targeted manner.

This data validates the hypothesis that targeting antigens to particular immune cells is beneficial over administration of the antigen in the absence of targeting. It will be clear that the OVA antigen used here, the Z33 tag used here, and the CD40 binding domains used here can be replaced with any antigen, tag, or immune cell binding domain.

REFERENCES

1. Sharma, P. and J. P. Allison, *The future of immune checkpoint therapy*. Science, 2015. 348(6230): p. 56-61.
2. Picco, G., et al., *Targeting DNGR-1 (CLEC9A) with antibody/MUC1 peptide conjugates as a vaccine for carcinomas*. Eur J Immunol, 2014. 44(7): p. 1947-55.
3. Zom, G. G., et al., *Two in one: improving synthetic long peptide vaccines by combining antigen and adjuvant in one molecule*. Oncoimmunology, 2014. 3(7): p. e947892.
4. Sanchez-Paulete, A. R., et al., *Cancer Immunotherapy with Immunomodulatory Anti-CD137 and Anti-PD-1 Monoclonal Antibodies Requires BATF3-Dependent Dendritic Cells*. Cancer Discov, 2016. 6(1): p. 71-9.
5. Reuter, A., et al., *Criteria for dendritic cell receptor selection for efficient antibody-targeted vaccination*. J Immunol, 2015. 194(6): p. 2696-705.
6. Chatterjee, B., et al., *Internalization and endosomal degradation of receptor-bound antigens regulate the efficiency of cross presentation by human dendritic cells*. Blood, 2012. 120(10): p. 2011-20.
7. Wang, W. W., et al., *Antigen targeting to dendritic cells with bispecific antibodies*. J Immunol Methods, 2005. 306(1-2): p. 80-92.
8. Yin, W., et al., *Functional Specialty of CD40 and Dendritic Cell Surface Lectins for Exogenous Antigen Presentation to CD8(+) and CD4(+) T Cells*. EBioMedicine, 2016. 5: p. 46-58.
9. Geert A. Daudey, Harshal R. Zope, Jens Voskuhl, Alexander Kros, and Aimee L. Boyle, *Membrane-Fusogen Distance Is Critical for Efficient Coiled-Coil-Peptide-Mediated Liposome Fusion*, Langmuir, 2017, 33, 12443-12452
10. Y. Yano, A. Yano, S. Oishi, Y. Sugimoto, G. Tsujimoto, N. Fujii and K. Matsuzaki, ACS Chem. Biol., 2008, 3, 341-345

---

The invention claimed is:

1. A complex comprising a polypeptide and a tagged antigen,
wherein the polypeptide comprises at least one immune cell binding domain and at least one tag binding domain,
wherein the at least one immune cell binding domain specifically binds to an immune cell target, and
wherein the at least one tag binding domain specifically binds to a tag, and
wherein the tagged antigen comprises the tag to which the tag binding domain of the polypeptide binds.

2. The complex of claim 1 wherein the antigen is a peptide, protein or fragment thereof that comprises an antigenic peptide or protein sequence.

3. The complex according to claim 2 wherein the antigenic peptide or protein sequence is a cancer antigen, optionally wherein the cancer antigen is a Human Papillomavirus (HPV)-associated cancer antigen.

4. The complex of claim 1 wherein the polypeptide comprises at least two tag binding domains capable of binding to at least two different tags, and wherein the complex comprises at least two tagged antigens.

5. The complex according to claim 1 wherein the antigen comprises an antigenic peptide or protein sequence that has been identified as a neoantigen that has arisen in a tumour or cell.

6. The complex according to claim 1 wherein the antigen comprises an antigenic peptide or protein sequence that is derived from a pathogen, optionally wherein the pathogen is a bacteria, fungus or virus, optionally wherein the virus is Human Papillomavirus (HPV).

7. The complex according to claim 1 wherein the tag is a peptide tag and wherein the peptide tag is not derived from tetanus toxin.

8. The complex according to claim 1, wherein the at least one tag binding domain is an Fc region of an antibody or antibody fragment or variant of an Fc region of an antibody or antibody fragment which specifically binds to a peptide tag.

9. The complex according to claim 1, wherein the tag binding domain binds to the Fc-binding peptide Z33

[SEQ ID NO: 51]
(FNMQQQRRFYEALHDPNLNEEQRNAKIKSIRDD).

10. A pharmaceutical composition comprising a complex according to claim 1.

11. The pharmaceutical composition according to claim 10 wherein the composition comprises more than one different complex,
optionally wherein the antigen in each complex is different and the tag is the same, optionally wherein the antigens are antigenic peptides or proteins and wherein the antigenic sequences of the tagged antigen(s) of each complex are different and the tag is the same in each complex; or
wherein the tag is different in each complex and the sequence of the antigenic peptides or proteins in each complex are different.

12. A method for the treatment or prevention of a disease wherein the method comprises administering a complex according to claim 1, optionally wherein said disease is cancer.

13. The method of claim 12 wherein said disease is pathogenic infection,
optionally wherein the method is for the treatment or prevention of a bacterial, fungal or viral infection, wherein the antigen comprises an antigenic peptide or protein sequence derived from a bacteria, fungus or virus, optionally from Human Papillomavirus (HPV).

14. The method of claim 12
wherein the antigen comprises an antigenic peptide or protein sequence that has been identified as a neoantigen that has arisen in a cell, optionally a tumour cell; or a cancer protein or peptide antigen.

15. The method of claim 12, wherein a peptide or protein neoantigen has been identified as having arisen in the patient, and wherein the tagged antigen comprises the neoantigen peptide or protein sequence.

16. The method according to claim 15 wherein the method further comprises the initial step of identifying a neoantigen that has arisen in a patient.

17. A method of producing a complex according to claim 1, wherein the method comprises contacting the polypeptide with a tagged antigen in vitro.

18. An in vitro or ex vivo method of activating an immune cell, wherein the method comprises contacting the immune cell with a complex according to claim 1, wherein the immune cell comprises the immune cell target to which the immune cell binding domain of the polypeptide binds.

19. A polypeptide comprising at least one immune cell binding domain and at least one tag binding domain,
wherein the at least one immune cell binding domain is capable of specifically binding to an immune cell target; and
wherein the at least one tag binding domain is capable of specifically binding to a tag, optionally a peptide tag, wherein the peptide tag is not derived from tetanus toxin.

20. A complex formed by contacting a polypeptide with a tagged antigen in vitro,
wherein the polypeptide comprises at least one immune cell binding domain and at least one tag binding domain,
wherein the at least one immune cell binding domain specifically binds to an immune cell target, and
wherein the at least one tag binding domain specifically binds to a tag, and
wherein the tagged antigen comprises the tag to which the tag binding domain of the polypeptide binds, optionally wherein the tag is a peptide tag.

* * * * *